US008118751B2

(12) United States Patent
Dobak, III

(10) Patent No.: US 8,118,751 B2
(45) Date of Patent: Feb. 21, 2012

(54) DEVICES AND METHODS FOR ACCELEROMETER-BASED CHARACTERIZATION OF CARDIAC FUNCTION AND IDENTIFICATION OF LV TARGET PACING ZONES

(75) Inventor: John D. Dobak, III, La Jolla, CA (US)

(73) Assignee: CardioSync, Inc., La Jolla, CA (US)

( * ) Notice: Subject to any disclaimer, the term of this patent is extended or adjusted under 35 U.S.C. 154(b) by 255 days.

(21) Appl. No.: 12/396,420

(22) Filed: Mar. 2, 2009

(65) Prior Publication Data
US 2010/0049063 A1 Feb. 25, 2010

Related U.S. Application Data

(63) Continuation of application No. 11/318,325, filed on Dec. 23, 2005, now abandoned.

(60) Provisional application No. 60/650,532, filed on Feb. 7, 2005, provisional application No. 60/655,038, filed on Feb. 22, 2005, provisional application No. 60/656,307, filed on Feb. 25, 2005, provisional application No. 60/657,766, filed on Mar. 1, 2005, provisional application No. 60/659,658, filed on Mar. 8, 2005, provisional application No. 60/663,788, filed on Mar. 21, 2005, provisional application No. 60/669,324, filed on Apr. 7, 2005, provisional application No. 60/677,569, filed on May 4, 2005, provisional application No. 60/680,673, filed on May 13, 2005.

(51) Int. Cl.
*A61B 5/04* (2006.01)
(52) U.S. Cl. ........................................ 600/528
(58) Field of Classification Search ............ 607/17, 607/18, 24; 600/528
See application file for complete search history.

(56) References Cited

U.S. PATENT DOCUMENTS

| 3,695,253 A | 10/1972 | Vielhauer |
| 4,496,361 A | 1/1985 | Kilkson |
| 4,763,645 A | 8/1988 | Kapp |
| 5,031,614 A | 7/1991 | Alt |
| 5,268,777 A | 12/1993 | Sato |

(Continued)

OTHER PUBLICATIONS

J.C. Wood et al., "Time-Frequency Transforms: A New Approach to First Heart Sound Frequency Dynamics", IEEE transactions in Biomedical Engineering, vol. 39, No. 7, Jul. 1992, pp. 730-740.

(Continued)

*Primary Examiner* — Scott Getzow
*Assistant Examiner* — Amanda Patton
(74) *Attorney, Agent, or Firm* — Mark D. Wieczorek; Meyer & Williams P.C.

(57) ABSTRACT

Systems according to the invention employ an acceleration sensor to characterize displacement and vibrational LV motion, and uses this motion data to characterize the different phases of the LV cycle for analyzing LV function. Systems may identify a target pacing region or regions in the LV or RV using the acceleration sensor by localizing regions of late onset of motion relative to the QRS, or isovolumic contraction, or mitral valve closure, or by pacing of target regions and measuring LV function in response to pacing. Systems further provide an implantable or non-implantable acceleration sensor device for measuring LV motion and characterizing LV function. An implantable myocardial acceleration sensing system ("IAD") includes at least one acceleration sensor, a data acquisition and processing device, and an electromagnetic, e.g., RF, communication device. The IAD may be integrated into the pacing lead of a CRT device and can operate independently of the CRT IPG.

9 Claims, 32 Drawing Sheets

U.S. PATENT DOCUMENTS

| | | | |
|---|---|---|---|
| 5,304,208 | A | 4/1994 | Inguaggiato et al. |
| 5,383,473 | A | 1/1995 | Moberg |
| 5,425,750 | A | 6/1995 | Moberg |
| 5,454,838 | A | 10/1995 | Vallana et al. |
| 5,496,351 | A | 3/1996 | Plicchi et al. |
| 5,496,361 | A | 3/1996 | Moberg |
| 5,540,727 | A | 7/1996 | Tockman et al. |
| 5,549,650 | A | 8/1996 | Bornzin et al. |
| 5,554,177 | A | 9/1996 | Kieval et al. |
| 5,628,777 | A | 5/1997 | Moberg et al. |
| 5,715,827 | A | 2/1998 | Corl et al. |
| 5,792,195 | A | 8/1998 | Carlson et al. |
| 6,002,963 | A | 12/1999 | Mouchawar et al. |
| 6,053,913 | A * | 4/2000 | Tu et al. .................. 606/41 |
| 6,077,236 | A | 6/2000 | Cunningham |
| 6,275,724 | B1 | 8/2001 | Dickinson et al. |
| 6,542,775 | B2 | 4/2003 | Ding et al. |
| 6,643,548 | B1 | 11/2003 | Mai et al. |
| 6,650,940 | B1 | 11/2003 | Zhu et al. |
| 6,665,564 | B2 | 12/2003 | Lincoln et al. |
| 6,667,725 | B1 | 12/2003 | Simons et al. |
| 6,705,999 | B2 | 3/2004 | Yu et al. |
| 6,885,889 | B2 * | 4/2005 | Chinchoy .................. 607/9 |
| 7,117,035 | B2 | 10/2006 | Wagner et al. |
| 7,248,923 | B2 * | 7/2007 | Maile et al. .................. 607/17 |
| 7,270,634 | B2 | 9/2007 | Scampini et al. |
| 2002/0016615 | A1 | 2/2002 | Dev et al. |
| 2003/0105496 | A1 | 6/2003 | Yu et al. |
| 2004/0019365 | A1 | 1/2004 | Ding et al. |
| 2004/0172078 | A1 | 9/2004 | Chinchoy |
| 2004/0172079 | A1 | 9/2004 | Chinchoy |
| 2004/0260346 | A1 * | 12/2004 | Overall et al. .................. 607/4 |
| 2005/0027320 | A1 | 2/2005 | Nehls et al. |

OTHER PUBLICATIONS

Anthony F. Rickards et al., "An Implantable Intracardiac Accelerometer for Monitoring Myocardial Contractility", PACE, Dec. 1996, vol. 19, pp. 2066-2071.

Rainee N. Simons et al., "RF Telemetry System for an Implantable Bio-MEMS Sensor", NASA/TM-2004-212899, Jun. 2004, 4 pages.

* cited by examiner

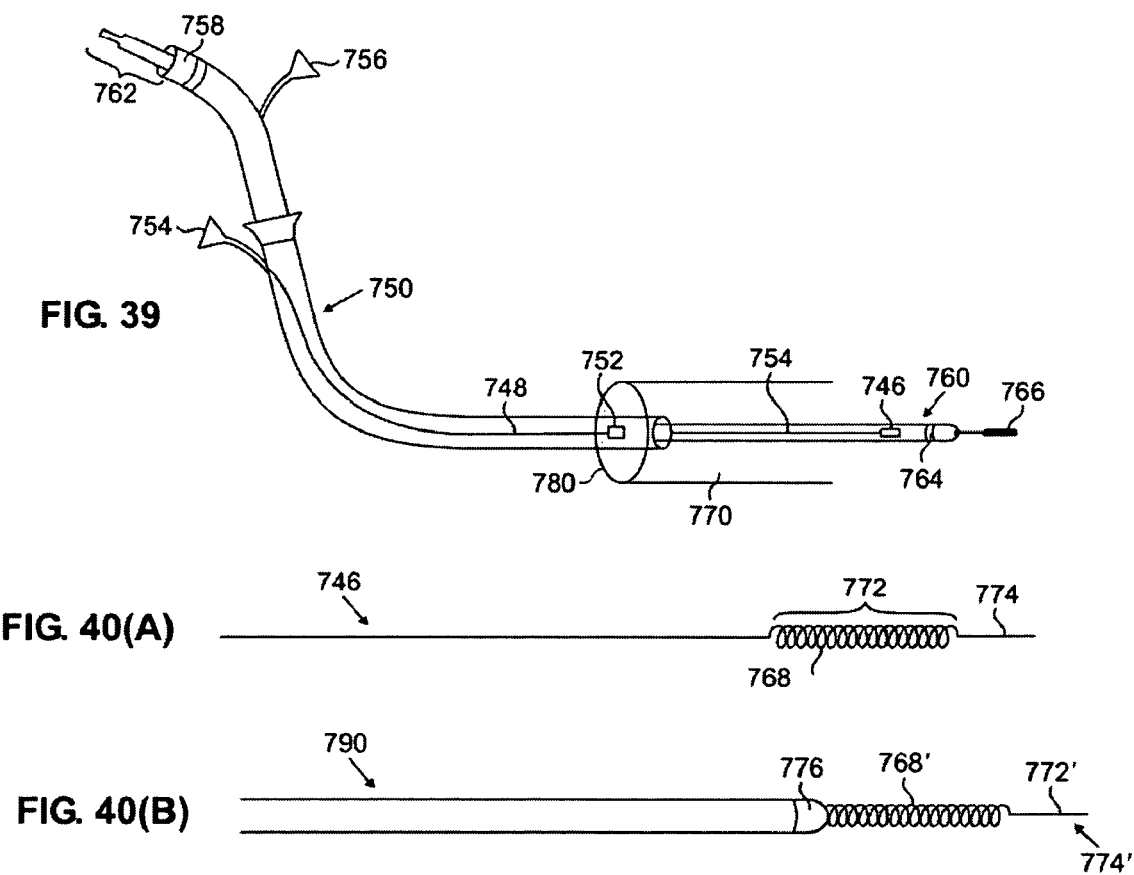

DEVICES AND METHODS FOR ACCELEROMETER-BASED CHARACTERIZATION OF CARDIAC FUNCTION AND IDENTIFICATION OF LV TARGET PACING ZONES

REFERENCE TO CONTINUING APPLICATIONS

This application is a continuation of U.S. patent application Ser. No. 11/318,325, filed Dec. 23, 2005 now abandoned, entitled "Devices and Methods For Accelerometer-Based Characterization of Cardiac Function and Identification of LV Target Pacing Zones, which claims the benefit of U.S. Provisional Application No. 60/650,532, filed Feb. 7, 2005, U.S. Provisional Application No. 60/655,038, filed Feb. 22, 2005, U.S. Provisional Application No. 60/656,307, filed Feb. 25, 2005, U.S. Provisional Application No. 60/657,766, filed Mar. 1, 2005, U.S. Provisional Application No. 60/659,658, filed Mar. 8, 2005, U.S. Provisional Application No. 60/663,788, filed Mar. 21, 2005, U.S. Provisional Application No. 60/669,324, filed Apr. 7, 2005, U.S. Provisional Application No. 60/677,569, filed May 4, 2005 and U.S. Provisional Application No. 60/680,673, filed May 13, 2005. Each of the prior US Provisional Patent Applications is incorporated by reference in its entirety herein.

BACKGROUND

The human heart delivers oxygenated blood to the organs of the body to sustain metabolism. The human heart has four chambers, two atria and two ventricles. The atria assist with filling of the ventricles, which pump blood to the body and through the lungs. The right ventricle (RV) pumps blood through the lungs to be oxygenated and the left ventricle (LV) pumps the oxygenated blood to the body.

A graph of the cardiac filling and pumping cycle and valvular events is shown in FIGS. 1a and 1b. The cardiac LV pumping cycle (LV cycle) is divided into two periods: diastole 52 and systole 54. Diastole 52 is the filling period and systole 54 is the ejection period. Five different phases of the LV cycle can be identified within the systolic and diastolic periods: isovolumic contraction 56, ejection 58, isovolumic relaxation 62, early diastolic filling (rapid filling) 64, and late diastolic filling (atrial contraction) 66. Mitral valve closure 68 ("MVC") occurs during isovolumic contraction and aortic valve closure 72 ("AVC") occurs during isovolumic relaxation. Also shown in the figures are the left ventricular pressure LV Press 74, a regular electrocardiogram ECG 76, the left ventricular end-diastolic volume LVEDV 78, the left ventricular end-systolic volume LVESV 82, a graph depicting heart sounds 84, the left atrial pressure LA Press 86, the aortic pressure 88, a-wave 92, c-wave 94, and v-wave 96.

Myocardial activation and systolic contraction is initiated in the atria by a regular electrical depolarization wave that spreads from the sinoatrial node to the ventricles at a normal resting cycle of 60 to 80/minute. Cardiac electrical activity can be sensed using a body surface electrocardiogram or ECG. The depolarization of the atria is sensed as a P-wave 98 on the ECG. A delay in depolarization between the atria and ventricles occurs and is measured on the ECG as the PR interval 102. Ventricular contraction and myocardial shortening starts at the interventricular septum and rapidly spreads to the posterior and lateral wall via the Purkinje system. Electrical depolarization that leads to ventricular contraction is measured on the ECG by the QRS complex 104. Following the QRS complex 104 is the T-wave 106, which reflects ventricular repolarization.

In the normal heart, a short delay from interventricular septal contraction to posterior-lateral contraction of approximately 20-40 ms occurs such that the lateral free wall is typically the first region of the heart to undergo shortening. Aortic valve closure signifies the end of the ejection phase of systole and the start of diastole. Diastole results in filling of the ventricles with blood and lengthening of the myocardium. In the normal heart diastole is typically longer than systole with the ratio dependent on heart rate.

LV myocardial motion is complex and includes both vibration and displacement (lengthening and shortening). Displacement occurs primarily along the longitudinal axis (base to apex), but there is also some radial displacement as well as clockwise and counterclockwise rotation. Displacement of the entire heart can also be caused by respiration. Superimposed on the large amplitude displacement motion is low amplitude vibrational motion related to isovolumic contraction/relaxation, valve closure, and valve pathologies such as mitral regurgitation.

The origin of LV displacement motion can be traced to the specific orientation and arrangement of muscle fibers in the myocardium. Vibrational motion of the LV is thought to be caused by acceleration and deceleration of the blood and turbulent blood flow. Studies of myocardial architecture have shown that the fibers are situated transverse and diagonal in a helical pattern. Transverse circumferential fibers are present in the base and midwall of the myocardium and produce radial narrowing of the ventricle. Systole starts with the development of tension primarily in the circumferential fibers, which stiffens and narrows the ventricle, and causes primarily radial displacement. The start of systole coincides with the isovolumic contraction phase of the LV cycle and also causes a vibrational motion thought to be related to directional changes of the blood and the accompanying acceleration/deceleration. Mitral valve closure also occurs during this isovolumic contraction period. Circumferential shortening is followed by longitudinal-diagonal fiber shortening resulting in primarily longitudinal displacement of the LV (base toward the apex) and ejection of blood. The action of these fibers also creates a rotation of the heart. This coincides with the ejection phase of the LV cycle. Mitral regurgitation is prominent during this ejection phase. Following ejection, lengthening and rotation in the opposite direction begins, and the isovolumic relaxation phase of the LV cycle occurs. Isovolumic relaxation is also thought to be associated with vibrational motion related to the acceleration/deceleration of the blood. Aortic valve closure also occurs during this phase. Early rapid filling of the LV with blood, as well as late filling, causes radial and longitudinal lengthening of the LV.

This motion of the ventricular myocardium and the LV cycle phases can be measured at the mitral annulus which is displaced radially and longitudinally. In addition, some rotation and the vibrational motion is transmitted at the annulus. Longitudinal displacement is an integral part of the global contractile function and has a good correlation with the overall ejection performance and diastolic filling performance of the ventricle.

Heart failure or cardiomyopathy is a medical syndrome characterized by deterioration of cardiac pumping performance. The primary deterioration is a progressive loss of heart muscle compliance and contractility. Loss of pump function leads to cardiac dilation, blood volume overload, pulmonary congestion, and ultimately organ failure. Symptoms of heart failure include orthopnea, dyspnea on exertion, cough, fatigue, and fluid retention. Many heart failure patients suffer from functional mitral regurgitation that can worsen with exercise and contributes to the progression of the disease. Lastly, patients with cardiomyopathy are prone to rhythm disturbances such as interventricular and intraventricular conduction delays leading to mechanical dyssynchrony, and tachyarrhythmias.

In cardiac pathology, such as heart failure, electrical conduction between atria and ventricles can be delayed excessively such that pumping function of the heart deteriorates. In addition, conduction delays in the spread of ventricular depolarization thwart the uniform spread of ventricular contraction and result in asynchronous ventricular shortening and a deterioration of performance. Some of the ventricular depolarization delays are due to abnormalities of the Purkinje system and are referred to as left or right bundle branch blocks (LBBB or RBBB). Bundle branch blocks are manifested by a wide QRS complex on the ECG.

A prolonged QRS, often manifested as an LBBB in patients with cardiomyopathy, is associated with poor prognosis. In several large clinical trials, lengthening of the QRS was independently associated with poor survival. In addition, several deleterious hemodynamic consequences arise in the presence of bundle branch block including shortening of the diastolic filling period, aggravation of mitral regurgitation, and abnormal systolic wall motion. The overall result is a typical and sometimes dramatic deterioration in cardiac performance.

Most therapies to improve cardiomyopathy are implemented and tailored empirically, or indirectly, based on patient symptoms, with little or no information on the mechanical optimization of cardiac pumping. In practice, assessment of mechanical pumping properties is difficult. Some information can be obtained by inserting catheters into the chambers of the heart, but these catheters cannot be left in chronically and it is impractical to subject patients to repeated procedures.

Objectives of cardiomyopathy therapy are to increase contractility, reduce afterload, i.e., the pressure against which the LV must pump, control blood and body water volume, blunt neurohumoral activation, improve cardiac compliance, increase ejection fraction, and reduce mitral regurgitation. Drugs, medical devices, and surgical treatments are employed to accomplish these goals and include diuretic drugs, blood pressure drugs, beta blocker drugs, cardiac pacing and resynchronization with or without tachyarrhythmia therapy, coronary artery bypass grafting, and heart transplantation.

Pacemaker therapy to treat heart failure is an established medical therapy. This therapy is employed to correct the dyssynchronous mechanical activity that occurs in heart failure by controlling the electrical activity of the heart. This form of pacing therapy is often referred to as cardiac resynchronization therapy or CRT. Dual chamber pacing (right atrium and right ventricle) to improve atrioventricular synchrony is a form of pacemaker therapy. Biventricular pacing is a newer approach that can improve cardiac function and mortality. Tachyarrhythmia and defibrillation therapy are also incorporated into the pacing therapy as heart failure patients often have problems with tachyarrhythmia. An experimental implantable pacing therapy for cardiomyopathy is cardiac contractility modulation ("CCM") in which a voltage potential or current is applied to the myocardium during the tissue's refractory period. This current improves myocardial contractility.

CRT is achieved by pacing (inducing myocardial activation) in the RV and LV, and has assumed prominence in patients with advanced heart failure and refractory symptoms. Specific candidates include patients with a prolonged QRS duration >120 milliseconds and/or LBBB. In newer approaches the RV and LV pacing is controlled and may occur at different intervals. LV free wall pacing only is also being explored.

Most clinical trials have demonstrated that about two-thirds of patients will have a clinical response to CRT as long as optimal pharmacologic therapy is maintained. Clinical responses include improvement in New York Heart Association functional class, improved exercise capacity, a decreased need for diuretic, reduced hospitalization for heart failure management, and the like. Unfortunately, about one-third of patients do not respond, and approximately 15% of patients can actually have a worsened clinical outcome.

In biventricular pacing or CRT, cardiac leads are placed in the right atrium (RA), the RV, and LV coronary veins via the coronary sinus. The leads have electrodes that can sense cardiac electrical activity and stimulate contraction in the myocardium. The leads are connected to a hermetically sealed, battery powered, programmable pulse generator and sensor/data storage device, termed here an "IPG" that is implanted subcutaneously.

Crucial to successful CRT is deployment of the left ventricular lead. This is typically accomplished by passing the LV lead through the coronary sinus into one of its venous tributaries overlying the epicardial left ventricular surface. Conventional pacing target sites are the posterior and lateral myocardium. In principle, the target site should be the segment of latest regional myocardial contraction relative to the QRS or some other measurement of the start of ventricular contraction. Although this is predicted to be in the posterior-lateral region, the actual site tends to be rather variable and difficult to predict in the individual patient. One other criterion for employing CRT is the identification of myocardial regions that contract in the post-systolic period, or in the period after aortic valve closure. Such regions are sometimes referred to as myocardial contractility reserve, because these regions of myocardium can add or contribute to systolic ejection if they can be forced to contract during systole. Pacing of regions can induce contraction and shortening of these late-contracting regions so that they contribute to systole. Consequently, any patient with a region of myocardium that contracts and deforms in the post-systolic period are candidates for CRT, regardless of the QRS interval.

Tissue Doppler and its corresponding myocardial velocity measurement have been used to measure various mechanical properties of ventricles and atria. Characterization of systolic and diastolic function can be performed. In addition, tissue Doppler has been employed in the assessment of mitral regurgitation and ischemia.

Tissue Doppler velocity measurements can detect tissue velocity changes, but these changes do not necessarily correlate with ventricular shortening which is required for cardiac pumping during systole. In an asynchronous ventricle, contraction may not be accompanied by shortening due to the effects of earlier-contracting segments on late-contracting segments. Newer techniques that employ measurements of cardiac strain and shortening are able to assess cardiac motion.

General strategies for LV lead placement can be developed with tissue Doppler imaging, a sophisticated echocardiographic technique, which allows visualization of individual myocardial segments and their contraction patterns, and allows visualization and analysis of segmental wall motion and velocity. It has been observed that up to 50% of patients may have the left ventricular lead, when placed in a conventional fashion pacing in a zone that does not correspond to the best myocardial contraction segment, i.e. there is a mismatch between the desired target and the actual target. Moreover, it is only those patients in whom a match occurred between the paced segment and the target zone where a clinical response was observed (only in about 30-50% of patients). This may explain why there is a lower than desired clinical response rate to CRT.

To improve CRT there is not only the need to identify target zones for pacing, but also to identify suitable patients. Further, a substantial percentage of patients with a normal or only slightly-widened QRS interval may also be candidates for CRT. Tissue Doppler scans can be suitable to measure ventricular dyssynchrony and therefore may be able to identify appropriate patients and optimize therapy. One measure of dyssynchrony identified with tissue Doppler is the assessment of peak velocity delays relative to the QRS onset of different myocardial segments and the standard deviation of these delays. However, tissue Doppler imaging requires specialists to perform the scan and can only be performed during a clinical visit. Thus, continuous or daily monitoring is not possible with this technique. Moreover, the complexity of the technique makes it too cumbersome to use during the LV lead placement.

Motion of the heart and LV, both displacement and vibration, can be measured directly with an acceleration sensor. This motion can be used to characterize the LV cycle phases. Integration of the acceleration measurements during displacement provides myocardial velocity data that may closely parallel tissue Doppler imaging velocity measurements. Double mathematical integration of the acceleration sensor signal would allow characterization of the distance of displacement. Thus, an acceleration sensor-based system could be used to identify target regions of myocardium for pacing, optimize and characterize the regional and global LV response to pacing of the target region, and identify candidates for CRT, including those without a widened QRS. Since LV motion and cardiac pathologies such as mitral regurgitation occur at different frequencies, e.g., higher frequency vibration and lower frequency displacement, acceleration signals at different frequencies are ascertained. In this way, the complete LV cardiac cycle and cardiac pathologies can be characterized and monitored for changes due to pacing. An appropriately designed implantable myocardial acceleration sensing device (IAD) could monitor global and regional cardiac function long term, and would allow optimization of many treatment aspects of heart failure, including pharmacologic therapy. This monitoring may occur without the need for specialized personnel and scanning. Moreover, the appropriately designed system would allow characterization of the complete cardiac cycle (systole and diastole) and global monitoring of cardiac mechanical function.

Accelerometers have been used in pacemaker IPGs for rate control purposes (U.S. Pat. No. 5,383,473 and U.S. Pat. No. 5,425,750). A sensor implanted in the heart mass for monitoring heart function by monitoring the momentum or velocity of the heart mass is generally disclosed in U.S. Pat. No. 5,454,838. A catheter for insertion into the ventricle for monitoring cardiac contractility having an acceleration transducer at or approximately at the catheter tip is generally disclosed in U.S. Pat. No. 6,077,236. Implantable leads incorporating accelerometer-based cardiac wall motion sensors and for arrhythmia discrimination are generally disclosed in U.S. Pat. Nos. 5,628,777 and 6,002,963. Accelerometers used for discrimination of various cardiac arrhythmias are also generally disclosed in U.S. Pat. No. 5,268,777. Additionally, other disclosures have proposed the use of an accelerometer to optimize pacing timing, such as AV delay/interval and interventricular (V-V) timing (U.S. Pat. Nos. 5,549,650; 6,542,775; 5,549,650, 5,540,727 and U.S. Applications 2003/0105496 A1, 2004/0172079 A1, 2004/0172078 A1, and 2005/0027320 A1).

SUMMARY OF THE INVENTION

To the best of the inventor's knowledge none of the above disclosures proposes using acceleration sensors to characterize all components of LV motion, displacement and vibration, and to use this motion data to characterize the different phases of the LV cycle for analyzing LV function. These disclosures do not provide a means for separating out the displacement and vibrational components of LV motion, which occur at the same time, through different frequency sensing or filtering and analysis. Prior disclosures do not provide devices or methods for identifying the optimal myocardial pacing zone or region in the left or right ventricle for CRT, such as measuring the onset of motion relative to the onset of the QRS or isovolumic contraction or mitral valve closure. Prior disclosure do not provide a method for multiple catheter repositionings in the LV or coronary sinus or great cardiac vein to map the motion of the LV for identifying the optimal pacing region. Prior disclosures do not describe characterizing the response to pacing of a target region by measuring parameters indicative of r LV function (e.g., myocardial performance index or QRS onset to aortic valve closure). Prior disclosures also do not disclose measuring cardiac pathologies such as mitral regurgitation, which may be sensed as vibration motion at frequencies greater than about 150 Hz. Prior disclosures do not disclose a means for optimizing complete cardiomyopathy therapy, including drugs and devices, through the use of implantable acceleration devices. Prior disclosures do not provide a means for zeroing out gravity effects and tilt of the sensor. Prior disclosures do not define the use of capacitive acceleration sensors that integrate an inductive coil for wireless powering and data transmission.

Rather, prior disclosures typically describe a single acceleration sensor preferably disposed in the tip of an implantable pacing lead. For example, a single accelerometer is incorporated into the RV pacing lead to assess RV systolic activity and correlate the readings with RV dP/dt ("An implantable intracardiac accelerometer for monitoring myocardial contractility", PACE 1996, 19:2066-2071). The sensor is designed to detect only signals related to isovolumic contraction, and not the motion related to displacement or valvular pathologies. In another disclosure, an accelerometer is incorporated into an LV pacing lead for optimization of CRT timing intervals (US Application 2004/0172079 A1). This prior disclosure proposes to sense LV myocardial acceleration during isovolumic contraction and use this information to optimize the atrioventricular delay and the interventricular delay pacing signals. There is no disclosure on the use of an acceleration sensor device to identify target pacing regions and characterize the LV functional response to pacing. There is no disclosure on a means for characterizing both the displacement and vibration motion occurring at different frequencies. Consequently, the disclosure does not provide a way to monitor information on phases of the LV cycle that characterize LV function such as, displacement related to ejection, filling, afterload, volume status, and preload, nor can the same characterize vibration related to mitral regurgitation. Additionally, no disclosure is provided for integrating the acceleration signal to yield LV displacement velocity and distance measurements, which may provide additional information on LV contractile function. Also, neither disclosure nor device design is provided that would allow characterization of myocardial strain and strain rate.

In U.S. Patent Application 2003/015496 A1 single accelerometers are removeably disposed at the tip of CRT leads in the LV, RV and RA. A temporal phase shift between two different sensors is proposed to optimize CRT interventricular timing. Similar to the above, this disclosure generally describes interventricular interval optimization and does not provide a means for intraventricular target pacing region identification. Therefore it lacks disclosure on any means for identifying LV pacing region, means for identifying LV response to pacing, means for identifying LV dyssynchrony irrespective of QRS width, and characterization of LV motion and the phases of the LV cycle. Further, there is no disclosure for multi sensor integration into the same lead catheter, guidewire, or guide catheter/catheter system, and analysis of acceleration at different frequencies.

In one embodiment, the invention employs an acceleration sensor to characterize displacement and vibrational LV motion, and uses this motion data to characterize the different phases of the LV cycle for analyzing LV function. In another embodiment, the invention measures acceleration in at least two different frequencies with either two or more sensors or two or more frequency filters to characterize LV motion. In yet another embodiment, the invention senses high frequency (greater than about 150 Hz) low amplitude motion related to valvular pathology (e.g., mitral regurgitation), mid frequency (between about 20 Hz and 150 Hz) lower amplitude motion related to isovolumic contraction/relaxation and valve closure, and low frequency (less than about 20 Hz) high amplitude motion signals related to displacement of the LV occurring during the ejection phase and early and late diastole. In still a further embodiment, the invention identifies a target pacing region or regions in the LV or RV using an acceleration sensor by localizing regions of late onset of motion relative to the QRS, or isovolumic contraction, or mitral valve closure, or by pacing of target regions and measuring LV function in response to pacing. In another embodiment, the invention measures myocardial motion with an accelerometer relative to the onset of isovolumic relaxation or aortic valve closure to determine contractile reserve and/or the presence of post-systolic shortening. In yet another embodiment, the invention identifies target pacing regions in the LV using an acceleration sensor by pacing different regions and measuring the regional and/or global LV functional response to pacing. In still a further embodiment, the invention uses an acceleration sensor to measure LV function by sensing changes in the time interval length of the LV cardiac cycle phases (isovolumic contraction/relaxation, ejection, and/or filling); changes in mitral regurgitation signal amplitude and duration; and changes in peak amplitude and slope of isovolumic contraction, isovolumic relaxation, and ejection phases; and frequency changes of the isovolumic contraction and relaxation phases. In another embodiment, the invention may use an acceleration sensor to identify patients with LV dyssynchrony or asynchrony and a normal QRS width (90-120 ms), a modestly increased QRS width (120 to 150 ms), and wide QRS or LBBB pattern (QRS>150 ms). In yet another embodiment, the invention facilitates identification of the coronary ostium and LV vein branches into the coronary sinus for cannulation with guidewires or catheters. In a still further embodiment, the invention provides the physician with data from acceleration sensing for management of optimal pharmacologic treatment. In yet another embodiment, the invention provides a wireless acceleration sensing medical device and system for assessing LV motion and function.

Embodiments of the invention provide an implantable or non-implantable acceleration sensor device for measuring LV motion and characterizing LV function. An implantable myocardial acceleration sensing system ("IAD") includes at least one acceleration sensor, a data acquisition and processing device, and an electromagnetic, e.g., RF, communication device. The system may or may not have an internal battery. In one embodiment, an IAD is integrated into the pacing lead of a CRT device and can operate independently of the CRT IPG. In another embodiment, an IAD is used without a CRT to monitor heart failure. In this embodiment, at least one sensor is incorporated into an endovascular catheter that can be placed in the epicardial venous system of the LV.

In one illustrative system, the accelerometer sensors are micro-electromechanically ("MEM"s)-based to allow miniaturization, low-power consumption, and multiple-axis sensing. The sensor are conductively attached to the subcutaneously-implanted data acquisition and processing device, which is capable of RF telemetry communication and data transfer. The IAD monitors both vibrational and displacement LV motion during systole and diastole in at least the longitudinal axis. The IAD may also monitor LV acceleration in at least one location near the mitral annulus.

In another illustrative system, the IAD is integrated with a CRT device with a multi-electrode LV pacing lead. The IAD monitors LV motion and can dynamically adjust the electrodes that are used to pace. Similarly, the IAD can be integrated with or used with a CCM device to help monitor mechanical function and optimize therapy.

The IAD may perform data analysis algorithms that provide useful output for optimizing cardiomyopathy therapy. The output can be accessed by the multitude of physicians that are involved in cardiomyopathy management. These physicians include primary care physicians, internists, cardiologists, electrophysiologists, and cardiac surgeons. Statistical analysis of long-term data can identify periods in which cardiac function deviated significantly from baseline values or how the function changed with therapy.

IADs may also be implanted in the context of other cardiac procedures such as endovascular coronary procedures, electrophysiology procedures, coronary artery bypass grafting, and heart transplants. Thus, the patient is not subjected to an additional procedure. Integration of an IAD with a CRT or CRT pacing lead similarly offers the opportunity to optimize therapy and response in the context of a known and regularly performed procedure for cardiomyopathy.

In another embodiment, the sensor is a radiofrequency ("RF") MEMs accelerometer that incorporates coils that can inductively power or charge the sensor and transmit the data. Such an RF sensor provides long term, batteryless, wireless monitoring. Data from the wireless RF sensor may be acquired using an external antenna device that wirelessly couples to the sensor by directing electromagnetic energy of the appropriate frequency toward the sensor for inductive powering and/or data transmission. The antenna device is connected to a microprocessor-controlled display device that processes and stores the myocardial acceleration data for LV motion and therapy monitoring and optimization.

In another embodiment, one or more RF sensors can be directly implanted into or on the heart for LV motion or therapy monitoring or both. Alternatively, one or more RF sensors can be integrated into various devices that are implanted into the heart. In a further embodiment, one or more RF sensors are integrated into an endovascular catheter that can be inserted into the chambers or vessels of the heart. In another embodiment, one or more RF sensors are incorporated into a coronary stent. In still another embodiment, one or more RF sensors are incorporated into a cardiac pacing lead.

In still another embodiment, an LV motion mapping system is disclosed which can sense LV motion for optimizing CRT lead placement. The system may include an LV venous catheter, LV lead, guidewire, or guide catheter/catheter system with an acceleration sensor, connected to a signal processing and powering module, and a graphical display. The acceleration sensing catheter may be moved to different locations in the LV and used to identify regions of late systolic or post-systolic motion relative to a reference point such as the QRS, valve closures, or isovolumic contraction/relaxation. Alternatively, a pacing catheter or guidewire may be moved to different LV locations and an acceleration sensing catheter near the mitral annulus may measure changes in LV function due to pacing. Both techniques may be used to optimize CRT LV lead implantation. The mapping system may also be used to determine optimal RV pacing sites which may mitigate the need for placing an LV CRT lead.

Signals related to LV function include: earlier onset of motion relative to the QRS; the interval time length of the LV cycle including isovolumic contraction and relaxation, ejection, and filling; degree of mitral regurgitation; peaks of isovolumic contraction and relaxation; and the myocardial performance index. One or more sensors or one or more filters or both may be used to measure displacement or vibrational LV motion and the LV cycle phases, as well as valvular pathology.

BRIEF DESCRIPTION OF THE DRAWINGS

FIGS. 39, 40A and 40B show a guide catheter acceleration sensor for determining valve closure with an LV lead acceleration sensor for determining myocardial motion via differential frequency processing.

DETAILED DESCRIPTION

Figure 1A:
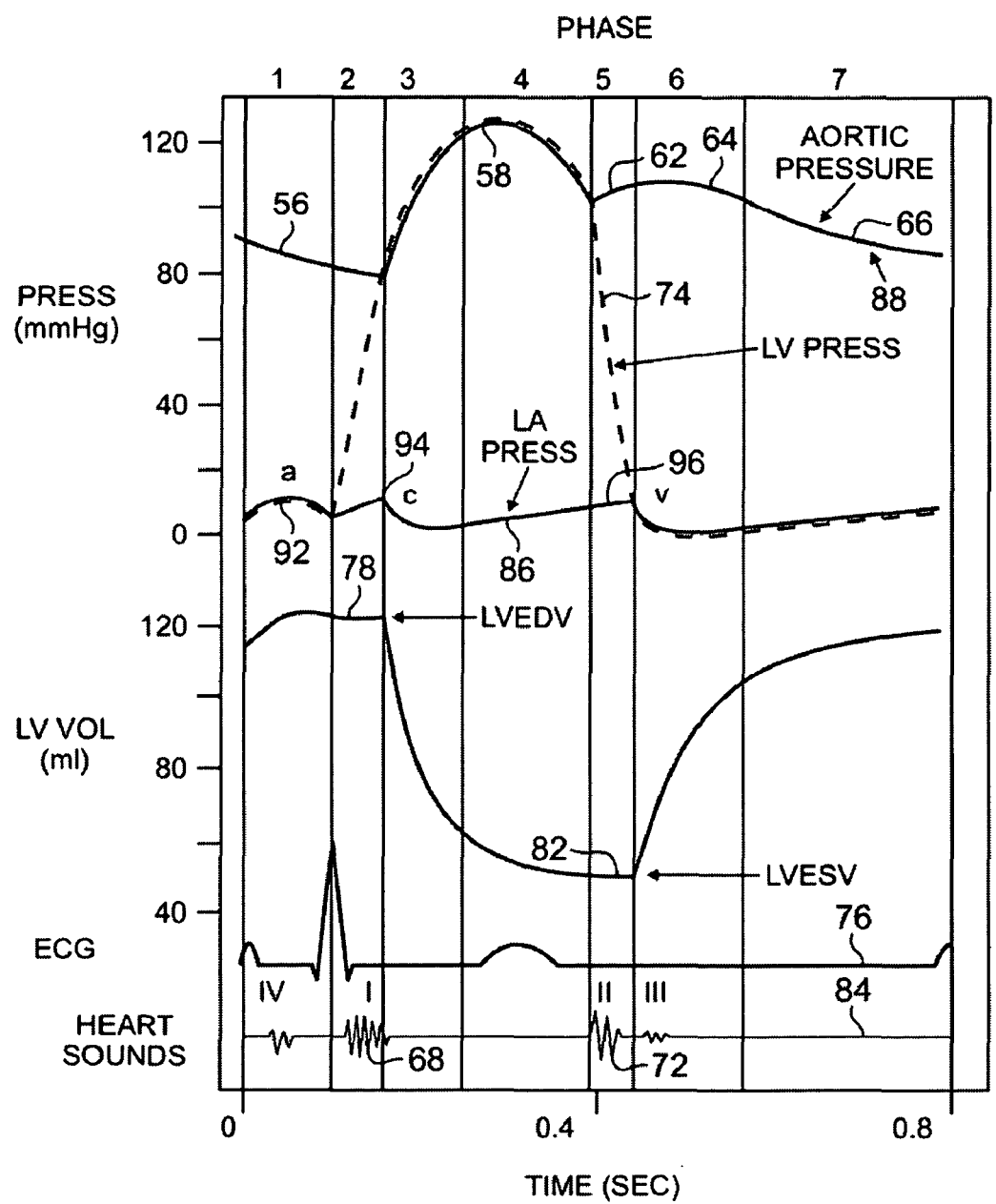
FIGS. 1A and 1B show graphs depicting various parameters of the cardiac pumping and ECG cycle.

Acceleration sensors are well-suited for measuring both vibration and displacement motions. They can be oriented along an appropriate axis to maximize the motion signal and to accurately measure the displacement. An acceleration sensor placed in or on the heart can measure vibrational or displacement components of heart motion, or both thereby allowing the characterization of pumping function and various pathologies.

The sensor may be based on MEMs principles, which allows for miniaturization and low power consumption. The design and fabrication of capacitance MEMs-based accelerometers are known to those skilled in the art. MEMs-based accelerometers are typically fabricated from silicon or semiconductor substrates. In one illustrative system, the sensor is fabricated from a radiation-resistant semiconductor as the sensor will be implanted in many cases under fluoroscopic guidance. The general design of the accelerometer measures capacitance changes due to the movement of a proof mass beam with a side arm interdigitated between two capacitor plates. As the proof mass beam and side arm move with acceleration or vibration, the capacitance changes and this signal can be output as a measure of motion. These accelerometers are fabricated from silicon substrates which allows for single-chip fabrication of the sensor with the necessary signal processing circuitry. This single-chip design increases the device's sensitivity as extremely small changes in capacitance can be measured. MEMs-based acceleration sensors as described above can measure milli- or even micro-Gs (1G equals 9.8 meters/sec$^2$) which is suitable for myocardial acceleration measurements which may typically measure between 50 and 500 milli-Gs or higher.

Other acceleration sensor designs could also be utilized and are known to those skilled in the art. For example, a thermal acceleration sensor could also be employed in which the proof mass is a gas. Also, while a multi-axis (2 or 3 axes) sensor may be most useful, single axis sensors could also be used and oriented appropriately to detect different axes of motion. It should also be noted that a pressure sensor can also sense motion and could be used in place of an acceleration sensor in certain systems when determining the onset of motion relative to reference points such as the QRS or isovolumic contraction of mitral valve closure.

Both the vibrational and displacement LV motion can provide useful information for diagnosis of CRT candidates and optimization of CRT therapy, as is described below. The sensors may be tuned to sense high-frequency, low-amplitude myocardial vibration, or low-frequency, high-amplitude displacement motion. Alternatively, the signal-processing filters could eliminate or reduce frequency bands that are lower or higher. For the purposes of this specification, high frequency signals are those greater than about 150 Hz and are related to vibrational motion and correspond to valvular pathologies such as mitral regurgitation; intermediate frequencies range between about 20 and 150 Hz can be used to sense vibrational motion and low-amplitude displacement motion related to isovolumic contraction or relaxation and valve closure (e.g., aortic and mitral); low-frequency signals are those with frequencies less than about 10 Hz or 20 Hz and are used to detect high-amplitude displacement, both lengthening and shortening, related to ejection and filling.

The frequency associated with the peak amplitude of valve closure is approximately 40-60 Hz. Thus, when sensing in the mid-frequency range, and to sense valve closure events, a narrower band may be used in this range than the typical mid-frequency range. This signal is closely related to isovolumic contraction and relaxation. Because many cardiac events such as isovolumic contraction and mitral valve closure, or LV shortening and mitral regurgitation, or LV lengthening and mitral valve opening, occur simultaneously, two or more sensors or two or more filters may be required to characterize these different cardiac signals. For the purposes of this specification, references made to the LV motion, LV cycle phases (e.g., isovolumic contraction or relaxation), and valvular phenomenon (e.g., aortic, pulmonic, or mitral closure or mitral regurgitation), should be assumed to be sensed with one or more sensors, in the appropriate axis, at the appropriate frequency. While this specification focuses on using valve closure events to provide reference points for characterizing target pacing regions and CRT optimization, valve opening could also be used.

Sensors can be oriented in the devices described below to optimally detect the desired LV motion. In one embodiment, a uniaxial sensor is oriented anatomically longitudinally (heart base to apex) to sense displacement of the LV. In addition, this sensor could detect vibrational motion through appropriate filtering. Alternatively, two uniaxial sensors oriented longitudinally and radially, i.e., toward the ventricular chamber, or three uniaxial sensor oriented longitudinally, radially, and coronally may be used. A single triaxial sensor could measure all these components. In another embodiment, two dual-axis sensors are oriented perpendicularly to each other in the catheter or LV-lead device. Three axes may be used for LV motion sensing with filtering used to detect motion at the appropriate frequency. The fourth axis may be used as to detect valvular events such as closure or high frequency pathologies such as mitral regurgitation. In still another embodiment, three dual-axis sensors may be oriented perpendicularly to each other with the three axes used to detect displacement motion and three axes used to detect mid- and high-frequency vibrations related to isovolumic contraction or relaxation and valvular pathology such as mitral regurgitation.

Implantable RF-Based Acceleration Sensor Devices

In one implantable embodiment, the MEMs-based sensor as described above also incorporates circuitry for electromagnetic (e.g., RF) inductive coupling to create an RF sensor, as shown in FIGS. 2-5.

Figure 2:
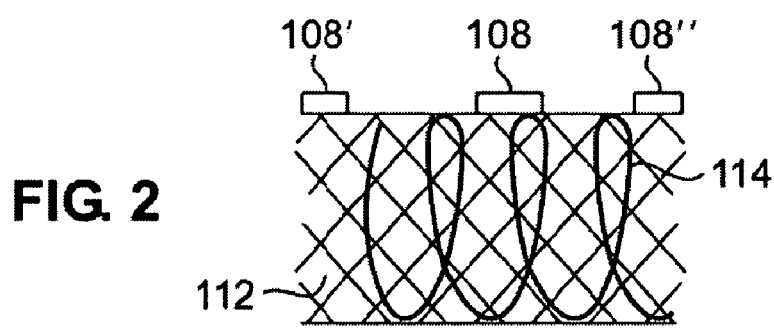
FIG. 2 shows a drawing of an acceleration sensor mounted to a coronary stent.
Figure 3:
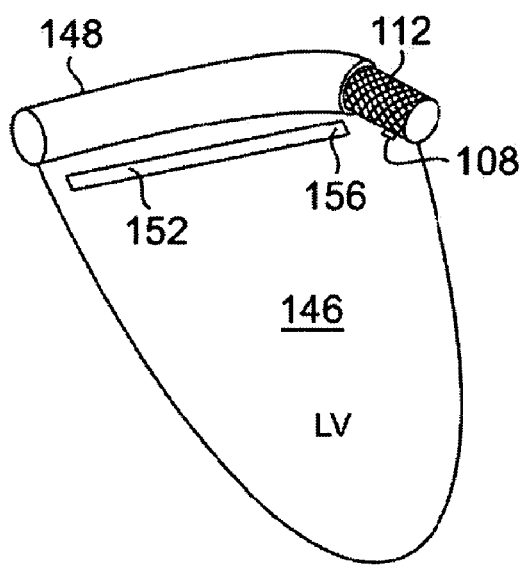
FIG. 3 shows placement during use of the sensor and stent of FIG. 2.

FIG. 2 shows the placement of a RF MEMS sensor 108 positioned on a coronary stent 112. A second sensor 108' may be employed at a fixed distance from sensor 108 for measurement of strain rate. An inductive coil 114 can further be integrated into the stent 112. A third or more sensors 108" may also be employed. This stent may be expanded in known fashion, employing a balloon. Referring to FIG. 3, the stent and sensor may be disposed at a lateral edge 156 of the mitral annulus 148 for wireless long-term monitoring of LV 146 function.

Figure 4:
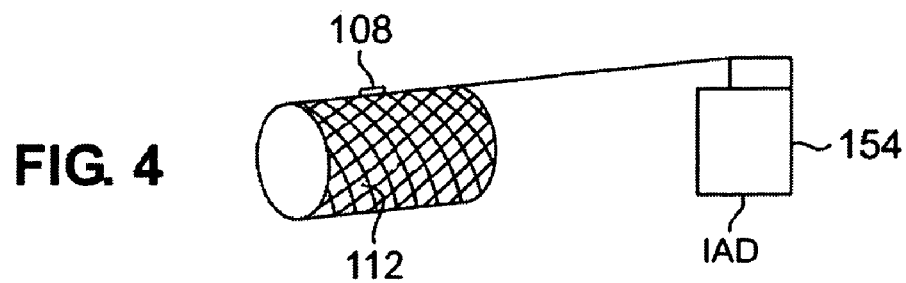
FIG. 4 shows an alternative configuration of the sensor and stent, in which the same are conductively coupled to an IAD.

In an alternative embodiment, shown in FIG. 4, the stent and sensor may be conductively coupled to an IAD 154, having a battery, signal processing capability, and data transmission circuitry and capability.

Figure 5:
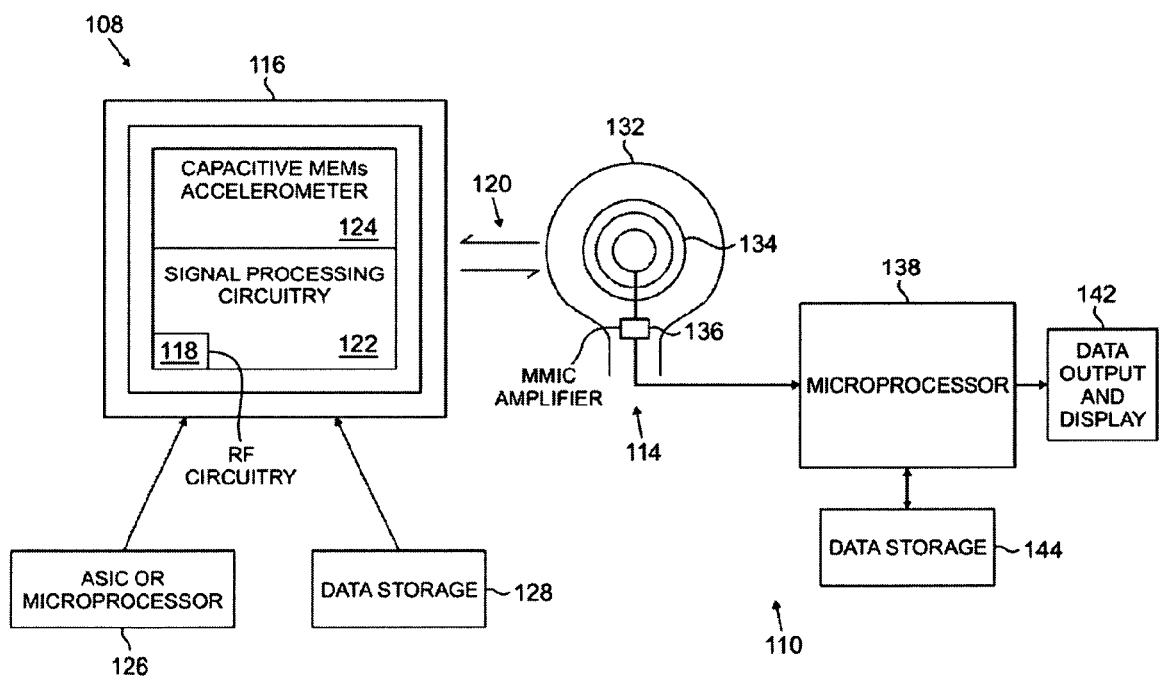
FIG. 5 shows a schematic of a system including a battery-less wireless acceleration sensor, an antenna wand, and a data acquisition and processing system.

In more detail, FIG. 5 shows a schematic diagram of a batteryless wireless acceleration sensor mounted to, e.g., a coronary stent, and a corresponding data acquisition and processing system. Referring to FIG. 3, an RF MEMs acceleration sensor 108, in an optional single chip design, is shown coupled via an RF transmission scheme 120 to a receiver system 114 which is in turn coupled to a data processing system 110. The RF transmission scheme 120 may be employed both for inductive powering and also for data transmission.

The MEMs acceleration sensor 108 includes an RF inductive coil 116 which may surround RF circuitry 118. RF circuitry 118 is coupled to signal processing circuitry 122. In another part of the chip, the capacitive MEMS accelerometer 124 is resident. As further indicated in the figure, a microprocessor, as an ASIC or otherwise, may be integrated onto the chip as well, along with optional data storage 128. Additional details of the MEMs acceleration sensor 108 design are given below.

The receiver system 114 includes a wand 132 which encloses an antenna 134 via which data and power are transmitted. An amplifier 136, such as a MMIC amplifier, may be employed to precondition the signal prior to transmission.

The data processing system 110 generally includes a microprocessor 138, a data output and display subsystem 142, and a data storage area 144.

A main component of the RF circuitry is the inductive coil which is used for data transmission and/or inductive powering. Alternatively, separate coils could be used for inductive coupling and data transmission. A representative silicon-etched inductive coil for powering capacitive MEMs sensors is disclosed in U.S. Pat. No. 6,667,725. The RF circuitry, including the inductive coil, may be incorporated into the same sensor chip. Alternatively this circuitry and coil may be fabricated separately and conductively linked to the sensor. For example, a planar RF antenna for inductive powering and data transmission may be fabricated on a flexible polymer substrate (e.g., polyimide) by winding or etching. The antenna may be planar. The sensor can be soldered to the flexible antenna circuit at bonding pad areas. The flexible polymer may then be wrapped around a vascular stent or incorporated into other cardiac devices and implanted into the body. In another embodiment a flat planar coil on a polyimide substrate is created with a long thin section. The planar coil can reside subcutaneously and the long thin section can reside transvenously within the body or within a device such as an LV pacing lead.

In addition, non-volatile memory may be used for storage of captured acceleration data. Similarly, this memory may be integrated into the same sensor chip, but may also reside as a separate chip and or in a separate location with appropriate connections. Lastly, a microcontroller or an application-specific integrated circuit (ASIC) may be incorporated into a sensor chip design or the same may reside on a separate chip and in a separate location. It should be noted that all device descriptions below that are based on RF coupling could be replaced with conductive element coupling for data transmission and power supply from a battery.

The RF accelerometer sensor can be hermetically sealed and packaged in a biocompatible housing to form a rugged sensor device for implantation into the body or cardiovascular system. Appropriate packaging may also reduce damage due to exposure to fluoroscopic radiation. Appropriate packaging would also not interfere with RF coupling. The device would have appropriate mechanisms for attachment to the body or cardiovascular system, including: tines, helical screws, suture pads, retention struts, and structures, such as porous titanium, to allow tissue ingrowth. There are various form factors the packaged accelerometer sensor device may have to facilitate implantation and various strategies for affixing the sensor device to the body.

An exemplary use of an RF sensor device is in cardiac surgery. Cardiac surgery and transplant patients can have severe myocardial dysfunction. An RF sensor could be affixed to the epicardial surface of the left or right ventricle. In this embodiment, the packaged sensor device may be circular and 2 cm or less in diameter and less than 5 mm thick. The device's epicardial surface may be flat and may have a helical screw for fixation into the myocardial tissue. Various polymeric materials maybe incorporated into the sensor epicardial surface to promote attachment to the myocardium. The upper device surface is curvilinear to conform to the chest wall. One or more sensors could be used to detect LV motion and related LV cycle phases, valve closure, and valve pathologies such as mitral regurgitation. Again, conductive elements and a battery supply could replace the RF components.

In another embodiment, an RF MEMs accelerometer sensor is incorporated into a coronary stent that is implanted in the LV arteries. The stent may also be implanted in the lateral coronary sinus or great cardiac vein or other LV veins near or proximate to the lateral edge of the mitral valve annulus. This is akin to implanting a sensor directly onto the epicardium and hence acceleration sensing of LV motion and the LV cycle phases can be measured. If two or more sensors are used separated by a known distance, strain and strain rate can be measured. The sensor or sensors could also be used to sense valve pathologies such as mitral regurgitation. Design and implantation of stents are known to those skilled in the art. The transceiver coil could be integrated into the stent body, or the stent body of a coiled stent design could serve as the transceiver, as shown in FIGS. 2 and 3. In still another embodiment, RF acceleration sensors are incorporated into a CRT or CCM pacing lead and preferably the LV lead. In this way, the sensor monitoring may occur independently of the CRT system via RF inductive powering and data transmission. RF acceleration sensors incorporated into a CRT lead or CCM lead could measure LV motion and characterize LV function, including valve pathologies such as mitral regurgitation, as described below. Additionally, RF MEMs sensors may be incorporated into guide catheters or guidewires for the same purpose.

RF sensor monitoring and data transfer could occur via an antenna device connected to a microprocessor which is worn by the patient or held near the sensor (e.g., over the chest). An appropriate antenna device would have a large enough antenna to inductively couple with the sensor. In one illustrative system, the antenna device may couple with the sensor at a distance of 5 to 15 cm and up to 15 feet. An exemplary antenna device is discussed in "RF telemetry system for an implantable bio-MEMs sensor", Rainee Simons, et al., NASA Glen Technical Reports, June 2004, NASA TM-2004-212899. As discussed in this paper, an MMIC amplifier connected to the antenna can allow for a reduction in the size of the sensor coil and the reader antenna.

The antenna would transfer the sensor data to a microprocessor or computing device that applies processing algorithms to the data and display the data to the physician for therapy monitoring. The microprocessor computing device and reader may be integrated into one device. Various signal processing functions may be carried out by the microprocessor such as filtering different bandwidths for different sensors to differentiate vibrational motion signals indicative of valve closure or mitral regurgitation from lower-frequency displacement motion related to LV ejection or filling. Because patients may have various valve anomalies, such as mitral regurgitation or aortic stenosis, the motion related to isovolumic contraction and relaxation may be especially monitored and may be indicative of valve closure events due to the short time period (about 10-30 milliseconds) between isovolumic contraction or relaxation and valve closure. Signals may be timed for detection after onset of the QRS, an endocardial electrogram, or other electrical signals. For example, sensing isovolumic contraction may occur immediately after sensing of the QRS for an interval of 50-150 ms, i.e., to allow particular attention to be given to this period. In addition, the microprocessor could carry out various statistical manipulations to monitor long-term trends. It should be noted that the microprocessor could also be located in an implantable device conductively coupled to the sensors.

Data transfer could be conducted by the physician periodically. Alternatively, the antenna device could be connected to the patient's home computer and transferred data could be sent to a physician or monitoring center over a network. An RF sensor-reading antenna integrated into or connected to a cellular phone would allow data to be wirelessly transmitted to a physician or monitoring center. Similarly a hand-held computing device with wireless communications could transfer sensor data wirelessly to a physician or monitoring center.

In another embodiment, at least one RF sensor, and even two or more, are incorporated into an endovascular catheter with or without a guidewire through lumen that can be implanted into the blood vessels of the body. In this illustrative system, at least one sensor is capable of sensing valve closure, isovolumic contraction or relaxation phases, or mitral regurgitation either by sensor tuning or filtering. This sensor catheter is placed via transvascular methods form the subclavian vein, internal jugular, or cephalic vein into the coronary sinus, or its tributaries, including the left ventricle drainage veins. The proximal portion of the catheter has a means for implantation and anchoring in the subcutaneous tissue.

Methods for inserting catheters into the coronary sinus and LV veins are well-known to those skilled in the art. In general, insertion occurs over a guidewire after accessing the coronary sinus ostium with a guide catheter. This placement is done under fluoroscopic visualization so the sensors are constructed to withstand the radiation exposure or are otherwise protected in a capsule that does not interfere with RF coupling. The catheter is flexible, may or may not be braided, and is made of a biocompatible polymer such as silicone or PBAX. The sensor catheter could have various features to facilitate placement and anchoring including fixed angles, a guidewire lumen, tines, and tip deflectability or steerability. In addition, the catheter may have an occlusion balloon and contrast injection lumen and port for acquiring an LV venogram. Alternatively the venogram features are incorporated into the guide catheter. Preferably, one sensor is located at the posterio-lateral or lateral edge of the mitral annulus. Additional sensors may be located on the catheter separated by known fixed distances (e.g. 5-10 mm) to provide strain and strain rate data. The above catheter allows long-term monitoring of myocardial mechanical activity and the LV cycle phases via wireless sensor powering and data transmission, thereby minimizing device complexity.

Preferably the region of the catheter where the sensors are located is suitably flexible to move with the displacement motion of the heart. Referring to FIG. 4, if two sensors are employed to measure strain or strain rate, the region between these two sensors should be suitably flexible to ensure that the two sensors move relative to each other during LV displacement. The sensors may, e.g., move radially and longitudinally relative to each other. The flexibility may be achieved by fabricating the region of the catheter where the sensors are located with a metallic or polymeric helical coil. Alternatively, a thin-walled polymeric catheter tubing could be employed. It may also important that the sensors lay adjacent to the myocardium as closely as possible or are prevented from moving within the vessel in a direction counter to the contracting or relaxing myocardium. This may be accomplished by weighting the bottom portion of the catheter where the sensors are located such that they lie flat on the myocardium.

Figure 6:
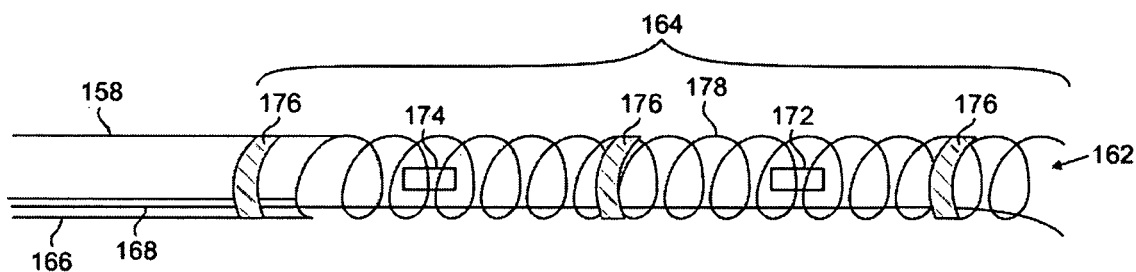
FIG. 6 shows an LV lead design to enhance flexibility between the sensors that detect myocardial strain or displacement.

For example, referring to FIG. 6, a system is shown including a catheter having a coiled sensor segment or LV lead design which enhances flexibility between the sensors for detecting myocardial strain or displacement. A catheter body 158 has a distal end 162 and adjacent to distal end 162 is sensor segment 164. A guidewire lumen 166 may accommodate a guidewire 168 for effective placement of the distal end 162 of the catheter. The sensor segment 164 includes a metallic or polymeric coil 178. A displacement sensor 172 may be mounted to the coil 178, along with a sensor 174 to detect valve closure or isovolumic phases or mitral regurgitation. One or more electrodes 176 may also be provided for sensing cardiac electrograms and delivering ablative RF energy if required.

Figure 7:
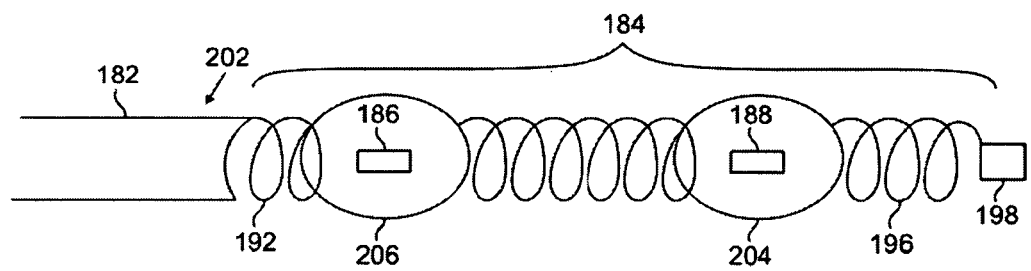
FIG. 7 shows an alternate coiled LV lead design with enhanced flexibility.

Alternatively, a structure can be used to constrain the sensors or sensor region of the catheter in the blood vessel, as shown in FIG. 7. This may be accomplished with a flexible wire cage that extends around the sensors or sensor region of the catheter at a diameter approximating or greater than the vessel diameter. An inflatable balloon or expanding deployable structure could also be used to constrain the sensors or sensor region of the catheter in the vessel. Lastly, angling or coiling may be employed of the region of the catheter with the sensors such that the bend helps constrain the sensor to the epicardium.

In particular, referring to FIG. 7, a system is shown in which a coiled sensor or LV lead design is disposed at the distal end of a catheter, the coiling allowing enhanced flexibility. A catheter body 182 has a sensor segment 184 at the distal end 202 thereof. A displacement-sensing sensor 188 is provided along with a sensor 186 which may measure valve closure, isovolumic phases, or mitral regurgitation. Coils 192, 194, and 196 provide enhanced flexibility for the sensor segment 184. It should be noted that the actual number of coils and sensors may vary depending on the design and requirements of the catheter. Coils 192, 194, and 196 may have a polymeric or metallic construction. Sensor 186 may be surrounded by a wire cage 206 which may be employed for constraining the sensor at a predetermined location in a vessel. Wire cage 204 may serve a similar purpose for sensor 188. The wire cages 206 and 204 further assist in preventing movement of the sensors during contraction.

Implantable Non RF-Powered Acceleration Sensor Devices

Figure 8:
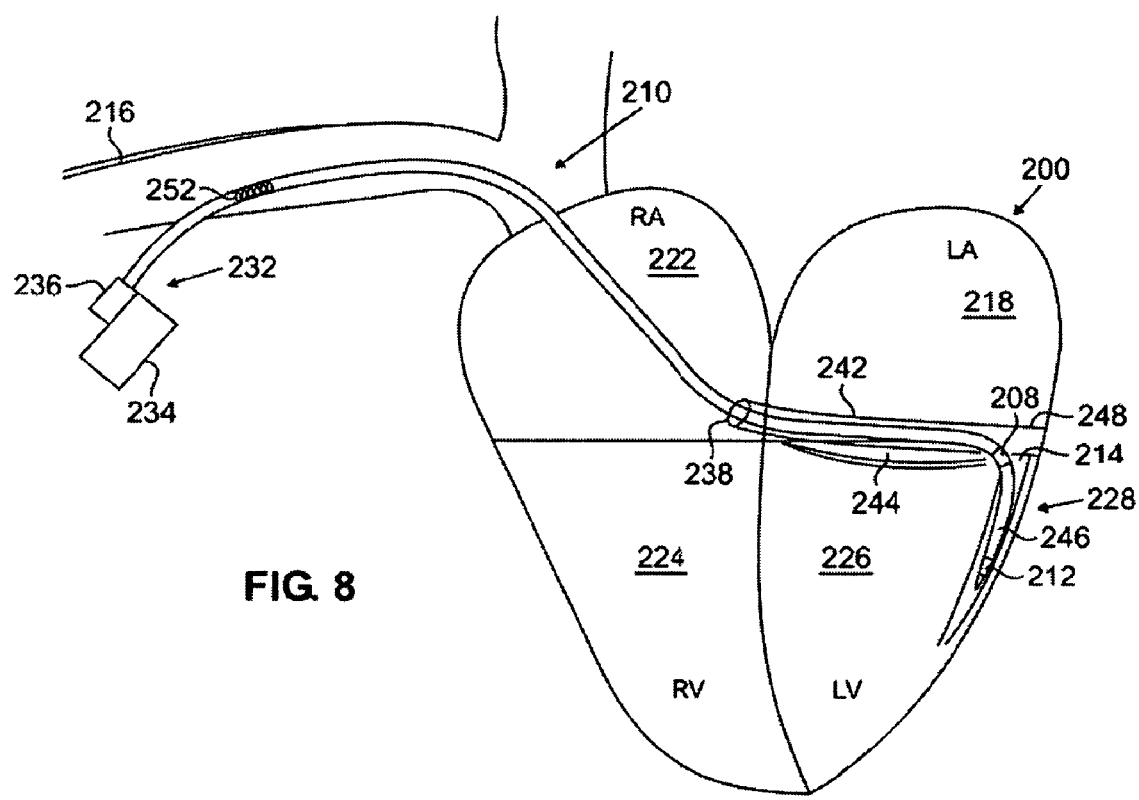
FIG. 8 shows an IAD device for long-term monitoring of LV mechanical performance.

In an alternative illustrative embodiment, and referring to FIG. 8, an IAD (is fabricated by incorporation of one or more non-RF MEMs acceleration sensors into an LV venous catheter, as previously described. In this system, long-term monitoring of LV mechanical performance can be performed. Acceleration related to both LV vibration and displacement, and valve pathologies such as mitral regurgitation, are measured by sensing at the appropriate frequency with the one or more sensors and employing filtering and signal processing.

In particular, FIG. 8 shows a heart 200 and subclavian vein 216. Also shown is the left atrium 218, the right atrium 222, the right ventricle 224, and the left ventricle 226. The catheter 210 may enter the heart through the subclavian vein 216, and extend through the coronary sinus ostium 38 into the coronary sinus 242 adjacent to which is the mitral annulus 244. After passing pathway through the coronary sinus, up to the cardiac vein 248, the catheter may extend into the LV vein 246.

The catheter 210 includes, near a first end 228, one or more sensors 208 and 212. For appropriate sensing, the sensors may be separated by an approximate pre-determined distance, e.g., 10 mm. One sensor may reside at the posterior-lateral edge 214 of the mitral annulus. The sensors may be conductively connected via the catheter 210, at a second end 232, to a subcutaneously-implantable data acquisition and processing device 234, which contains a battery supply, RF telemetry circuitry, a microprocessor, and data storage. The implantable data acquisition and processing device may be housed in a hermetically-sealed titanium shell. The processing unit 234 may connect to the catheter 210 via a proximal catheter connector 236. The sensors are encapsulated in a structure that protects them from fluoroscopic radiation damage; however, because the sensors in this embodiment are not directly RF-coupled, concerns about interfering with this coupling are eliminated. Insulated, multifillar, coiled wires 252, only a portion of which are shown in FIG. 8 for clarity, conductively connect the sensors to the proximal catheter connector 236. The connector attaches to the implantable data acquisition and microprocessor device 234, which powers the sensors, captures the sensor data, processes the data, and stores the data. The microprocessor controls the data sampling period and data sampling intervals. Captured acceleration data can be subjected to various data processing algorithms as are described below. This processed data can be stored in memory for later RF telemetry data transfer.

The battery in this embodiment may be rechargeable or typical of implantable battery sources. A typical implantable battery cell design is lithium silver vanadium oxide. Lithium carbon monoflouride may be also be used and has certain advantages due to its low weight.

Data storage may include readable and writable memory. A constant power input from the battery can allow volatile random access memory to be used for data storage and control functions. However, non-volatile data storage such as eeprom or flash may also be used. A combination of volatile and non-volatile memory storage may be used. Flash memory is non-volatile, compact and operates in the voltage range of implantable device batteries. Access to the data is rapid and megabyte storage capacity is available in a small size. Data may be stored on a first-in-first-out basis if memory becomes full prior to RF telemetry data transfer.

IAD acceleration data acquisition occurs over a sampling period that may be continuous or may be only a short period such as several seconds to up to 30 seconds or even several minutes. Data acquisition may occur at various sampling intervals such as from 8 to 1,440 times each day. Sensor data is sampled at rates sufficiently high to provide useful information for diagnosis and monitoring of CRT patients, target pacing regions, and heart failure (or cardiomyopathy) patients, and preferably at rates of 100 per second to 1000 per second. Sample rate, sample time, and interval periods are in part dependent on data storage capacity. Data captured and stored can be transferred by telemetry to a computing device either daily by the patient or weekly to monthly or longer by the physician. Data storage may be sufficient to allow at least one day of data storage and up to six months of data storage at the optimal data sampling rate, time, and interval to provide the physician with useful information.

Figure 9:
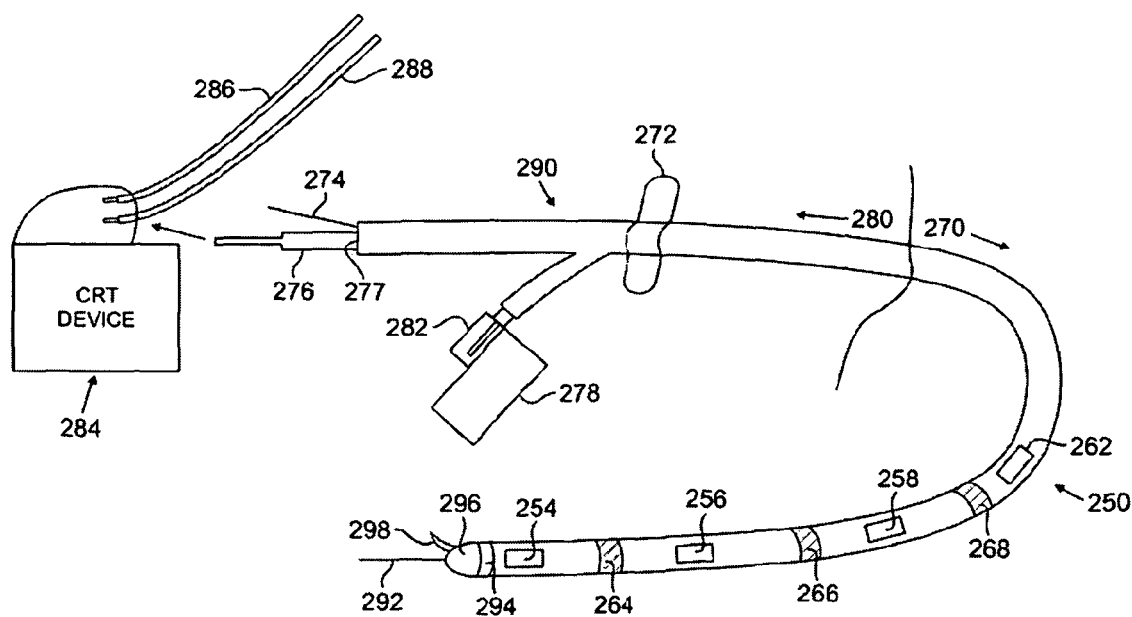
FIG. 9 shows an IAD integrated into an LV CRT pacing lead.

In another illustrative system the IAD described above is integrated with the proximal portion of a cardiac pacing lead, and preferably an LV CRT pacing lead, as shown in FIG. 9. At least one and possibly two sensors or more, shown as sensors 254-262, are incorporated into the LV pacing lead to measure LV motion and characterize LV function. The catheter may have an endovascular portion 270, and a subcutaneous portion 280, with a subcutaneous anchoring device 272 to anchor the adjacent portion of the catheter to the chest wall.

If strain or strain rate data is to be measured, two or more sensors may be incorporated at a known distance from each other, e.g., 5, 10, or 15 mm. One or more sensors are positioned on the lead as in the above embodiments with least one sensor residing at or near the posterior-lateral or lateral edge of the mitral valve annulus. The region of the lead between and around the sensors is made suitably flexible as previously described to ensure measurement of LV displacement and strain or strain rate. Sensing is carried out at different frequencies or with one or more sensors, or both, to measure both displacement and vibration to characterize the LV cycle phases and function, and pathologies such as mitral regurgitation. This IAD-integrated cardiac lead design allows cardiac mechanical monitoring independent of the CRT or CCM IPG. In this pacing lead embodiment, an implantable data acquisition and processor component 278 may be made as small as possible. Thus the battery cell used may be ultra miniature and may be rechargeable. Exemplary batteries are available from Quallion, Inc., of Sylmar, Calif., some of which have a 2.9 mm outer diameter cylindrical implantable battery (2.7-4.0 V, 3 mAmp-hours). A compact, non-volatile memory such as flash memory may be used in this system for processed data storage. Data processing algorithms may be performed after RF telemetry data transfer. The IAD RF telemetry may occur at a frequency that does not interfere with a CRT device 284. In addition to the battery power, data storage, and RF telemetry components, the implantable accelerometer data processor 278 may include a microprocessor, and may connect to the catheter via connector 282 at a distal end of Y-connector portion 290.

The catheter may be disposed using guide wire 274 having distal tip 292 adjacent tine 298, the guide wire being enclosed within a guidewire lumen (not shown).

Data and signals from the sensors and the data acquisition and processing component 278 are sent to the CRT device 284 via connector 276. The CRT device 284 may also receive signals from RA lead 286 and RV lead 288.

The design of LV pacing leads is known to those skilled in the art. In general, the LV CRT lead and fixation is similar to currently deployed leads with the exception of the requirement of accommodating the accelerometer-based sensors. The lead may be unipolar or bipolar. The conductive wires for the electrode may be coiled, mutifillar, and sheathed in a polymer such as silicone or polyurethane. A connector 276 at the proximal end 277 allows connection to the IPG and may be universal according to the IS-1 standard. A set of pacing electrodes 264-268 and 296 can be variously fabricated as a blunt-nosed tip (296), ring (264-268), or coiled. Non-corrosive alloys and metals can be used in the electrodes/lead such as platinum iridium or titanium iridium oxide or nickel cobalt or others such as are known in the art. The lead may elute a steroid drug via a drug elution component 294 to minimize inflammation at the electrode site location to keep capture thresholds lower. The lead could also have an ePTFE coating at the electrode to minimize fibrosis.

In another illustrative LV lead implantable system, a sensor 302 is incorporated into a sensor wire 304 that integrates with an implantable LV lead 300 (See FIGS. 10-14). This design allows the pacing lead to be positioned in the target pacing region and LV vein and the sensor can be positioned along the lateral or posterior edge of the mitral annulus. The sensor wire can also serve as a guidewire for the LV lead 300. The sensor 302 is attached to the sensor wire 304 via a stalk 306. The electrical conductors 308 of the sensor 302 run through the stalk 306 and down the length of the sensor wire 304. At the proximal end 310 of the sensor wire 304 is a connector 312 for linking the sensor 302 to an IAD 314. Even more proximal of end 310 may be a connector 342 to connecting the LV lead to a CRT device 344.

The sensor wire is integrated into the LV lead via a side wire lumen 316 along the length of the LV lead 300. The side wire lumen 316 is split to allow the sensor to be shuttled along the surface of the lead body 300. The sensor wire 304 may reside in the side wire lumen 316 and the sensor stalk 306 may reside along the split in the lumen 316. Thus the acceleration sensor 302 can be shuttled to the desired location at the mitral annulus 322 (see FIG. 14), such as near to the lateral border 326 of the mitral annulus 322, while the pacing lead 324 can go to the target pacing region, e.g., region 330. If the pacing lead 324 makes a bend to cannulate and LV branch that feeds into the coronary sinus, the sensor wire 304 can continue straight within the coronary sinus 326 or great cardiac vein to the desired location. In other words, the sensor can be placed in a desirable location for measuring LV function while the pacing lead is disposed in the proper location for pacing of the ventricle.

Figure 10:
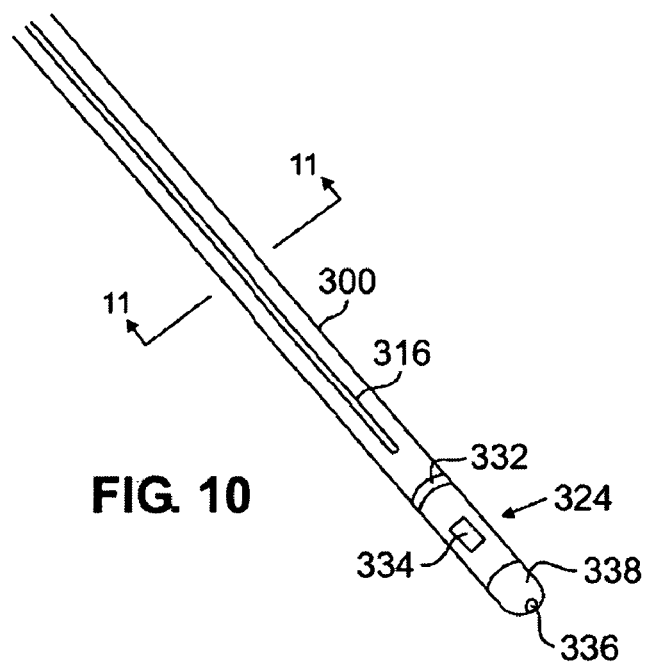
FIG. 10 shows an implantable LV lead with a sensor wire disposed such that it may be easily positioned at the mitral annulus edge.

Also shown in FIG. 10 is a central guide wire lumen 318 (which emerges from opening 336) that may be employed to position the LV lead 300, as well as components of the pacing lead 324, such as ring electrode 332, optional acceleration sensor 334, and microporous tip electrode 338.

In use, as the LV lead 300 bends to enter the posterior to lateral LV vein 342, the sensor wire 304 and sensor 302 bend out of the side lumen 316 due to the stiffness of the sensor wire 304. In this way, while the LV lead 300 goes into the LV vein 342, the sensor 302 continues on to a position near the mitral annulus or the lateral border thereof.

Figure 15:
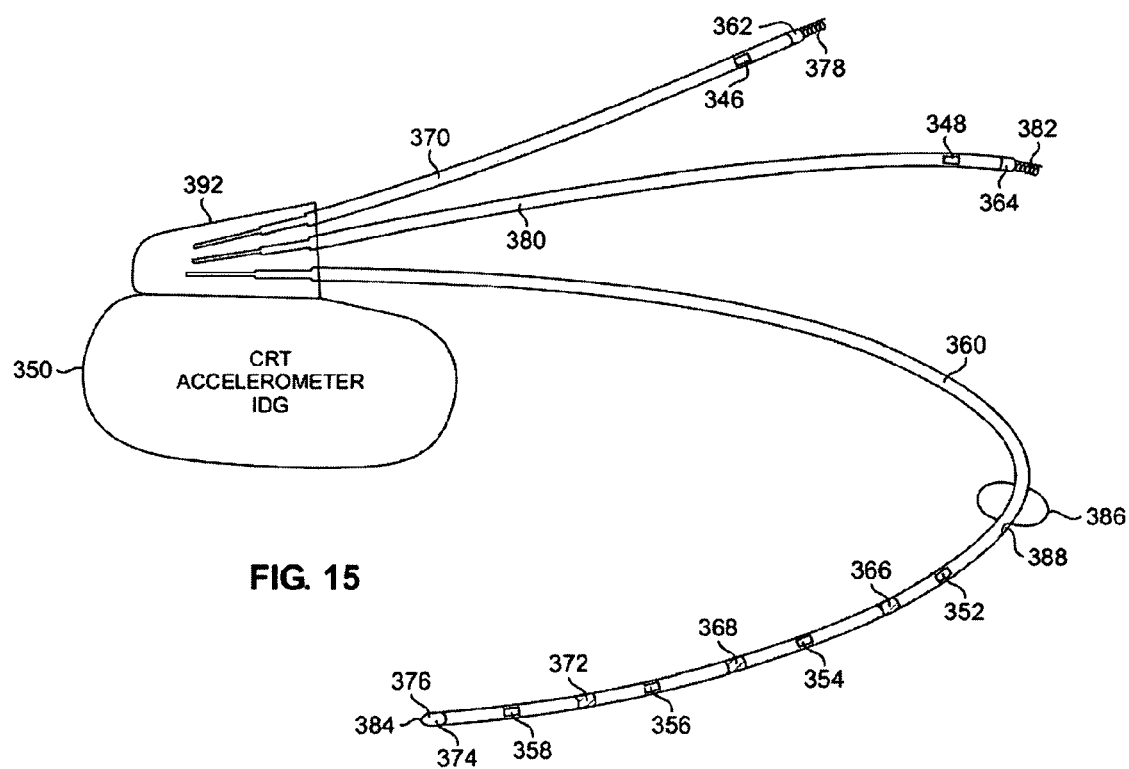
FIG. 15 shows a CRT acceleration sensing and control system.

In another illustrative system, as shown in FIG. 15, the IAD is integrated with the CRT or CCM IPG device, here shown as device 350 In this CRT acceleration sensing and control system, sensor data is used to control the output of pacing signals to electrodes in regions of late contraction and deformation.

As before, acceleration sensors 352-358 are integrated into the LV pacing lead 360. Circuitry and control of sensor data acquisition and processing may be integrated with the electronics of the CRT. Algorithm-processed acceleration data, described below, can be used to control and optimize the CRT such as via the atrioventricular interval, the interventricular interval, and may further be used to optimize the LV pacing site. Motion sensing may be used to dynamically change the pacing at multiple LV electrodes to continuously optimize the LV pacing over time. Cardiac events such as valve closure or isovolumic phases could control the timing, similar to a cardiac electrogram. At least one sensor may be designed to detect valve closure or isovolumic contraction and relaxation and may be positioned in the vessel to do so. Such a device that senses mechanical cardiac activity, e.g., valvular events, isovolumic contraction phases, and deformation, may be more optimal than controlling pacing signals with a sensed cardiac electrogram since cardiomyopathy causes mechanical dyssynchrony. Because some CRTs have defibrillation capability, the sensors and their attendant circuitry may have to withstand the energy delivered during a defibrillation event. This device may be capable of standard CRT functions, including multi-chamber EGM sensing, pacing, and trigger or inhibition control. Event sensing and storage would also be typical. Antitachyarrhythmia and bradyarrhythmia control of the atria and ventricles as is currently available may also be present and may include overdrive pacing, cardioversion and defibrillation. The device also allows periodic assessment of electrode capture threshold and adjustments to this threshold. This preserves battery life and ensures optimal myocardial activation and therapy. Hence myocardial deformation or strain rate may be monitored and pacing signals directed to the electrode where late deformation is occurring. Consequently, this type of CRT system may have an LV lead with multiple electrodes and acceleration sensors.

In more detail, device 350 may be connected to various leads via connector 392. The leads may be RA lead 370, RV lead 380, and LV lead 360. The RA lead 370 and the RV lead 380 may have optional acceleration sensors 346 and 348, as well as electrodes 362 and 364, and helical fixation points 378 and 382. Besides the acceleration sensors already noted on LV lead 360, a number of electrodes 366-374 may also be disposed. A guide wire lumen 384 may be disposed for use with a guide wire to aid is positioning the lead. The distal tip of the lead may include a tine 376 to help stabilize the lead in the vein. An optional balloon occluder 386 may be employed for venogram acquisition, with a contrast injection port 388 adjacent, but distal, thereto. The remainder of the catheter system is as has been already described.

Signal Processing, Data Analysis, and Monitoring

Figure 16:
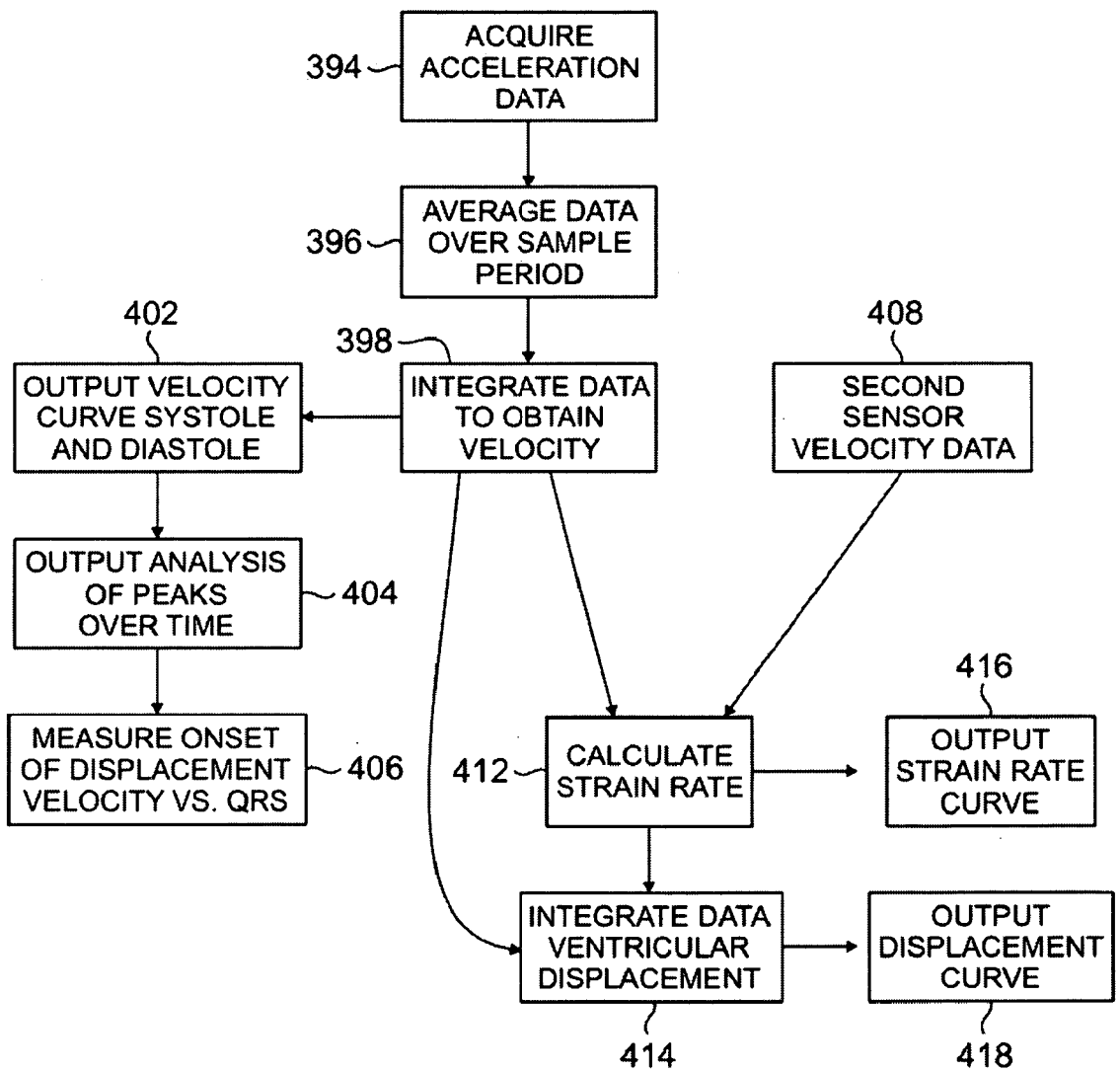
FIG. 16 shows a flowchart of a data processing algorithm.

In one illustrative system, the LV motion signals and data analysis are produced from a sensor along the mitral valve annulus. Mitral annular velocities have been shown to provide an accurate assessment of global left systolic and diastolic function. Mitral annular motion may also be best to measure displacement of the LV. Thus, this displacement motion may be subjected to a mathematical integration algorithm, as shown in FIG. 16, to yield velocity and distance.

In particular, the first step is to acquire acceleration data (step 394). Following this initial step, the data may be averaged over a predetermined sample period (step 396). The acceleration data may then be integrated to obtain the velocity (step 398).

A velocity curve may then be output to indicate systole and diastolic velocities (step 402). From this an analysis of peaks over time may be output (step 404). Finally, a measurement may be taken of the onset of displacement velocity versus the QRS peak (step 406).

If a second sensor acquires, or can be used to acquire, velocity data as well (step 408), displacement and strain rate may be obtained. From the first and second sensor velocity data, the strain rate can be calculated (step 412), and a strain rate curve may be output (step 416). From the strain rate and the velocity data, the data can be integrated to obtain the ventricular displacement (step 414), from which a displacement curve may be output (step 418). In general, LV motion signals may be processed in a manner best used for interpretation and therapy optimization. This includes analyzing indices or variables of LV function such as: peaks and slopes of acceleration, velocity, and distance curves, interval times of LV cycle phases, and analysis of pathological valve signals. Curves, such as a velocity curve of LV displacement, may be plotted with velocity in millimeters or centimeters/sec as the ordinate and cardiac cycle time in milliseconds as the abscissa. The algorithm may also involve calculating strain rate by processing acceleration data from at least two sensors separated by a known distance, e.g., 5 to 15 mm millimeters apart. Vibrational motion signals, e.g., that related to mitral regurgitation, may be presented as an amplitude and duration or a change in the frequency.

3-axis sensing is utilized in some illustrative systems. A more accurate measurement of peak amplitude can be measured by calculating the composite acceleration vector of each axis (x, y, and z). This can account for the gravitational acceleration and its effects on sensor tilting. The composite vector can be calculated by taking the square root of the sum of the x-axis measurement squared plus the y-axis measurement squared plus the z-axis measurement squared. This peak amplitude calculation can be applied to both the vibrational motion and the displacement motion. This may be particularly accurate during the implantation of an LV lead for CRT therapy when the patient is lying still on a procedure table. Here the sensor measures the peak in the LV veins or coronary sinus.

Thus, LV acceleration signals are sampled at a designated rate for a set time period, which is the sample period. Sensor data from the sample period can be averaged over several or more cardiac cycles to smooth out effects related to respiration and patient motion. The averaged data can then be used to produce a cardiac cycle acceleration curve which includes tissue acceleration, in, e.g., mm or cm/sec$^2$ versus cardiac cycle time, in milliseconds. This curve can then be mathematically integrated to produce a tissue velocity curve, e.g., in mm-cm/sec vs. cardiac cycle time. A second integration can performed to produce a distance curve, with units of mm or cm. Point-by-point acceleration sensing and integration can also be performed with peak identification, integration, and presentation as an individual data point rather than a curve.

Strain and strain rate curves and data points may be generated from velocity curves or data points. Generally at least two sensors are needed to measure strain rate. Velocity curves or data are generated from the two sensors in at least one axis. Strain rate or strain rate curves are created by integrating the difference in velocity data from the two sensors at the same point in the cardiac cycle and dividing this difference by the distance between the sensors $f(v_1-v_2)/l$. Since the distance of the sensors along the length of the implanted catheter or pacing lead is fixed, the distance between sensors is known. The strain curve is generated by integrating the strain rate curve.

Figure 17:
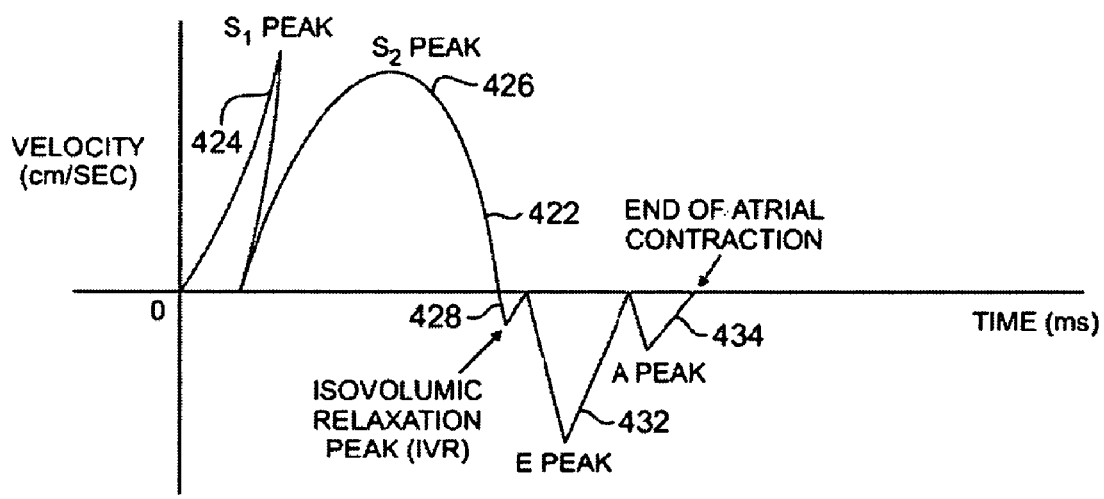
FIG. 17 shows a graph of velocity measured at the posterior-lateral edge of the mitral annulus.

Referring to FIG. 17, the velocity of LV displacement from the mitral annulus, generally at the posterior-lateral edge thereof, produces peaks representative of LV function during systole and diastole. Analysis of the peaks including: magnitude of the change, e.g., positive and negative, peak slopes, peak/peak ratios, slope/slope ratios, peak/slope ratios, and peak integration, provides specific information on LV function related to contractility, afterload, volume status, preload, ventricular compliance, ejection fraction, and ventricular synchrony. As above, FIG. 17 and the like may represent a composite of all three axes, x, y, and z, of the acceleration sensor.

This information is useful for the physician for long term management of the cardiomyopathic patient. This curve 422 often has two peaks during systole (S1 424 and S2 426) and three peaks during diastole (isovolumic relaxation 428, E 432, and A 434), though at times not all of the peaks are discernable. Trends in these peaks can provide useful information to the physician. These trends may prompt changes in pharmacologic therapy such as drug addition/elimination or dosage changes.

Figure 18:
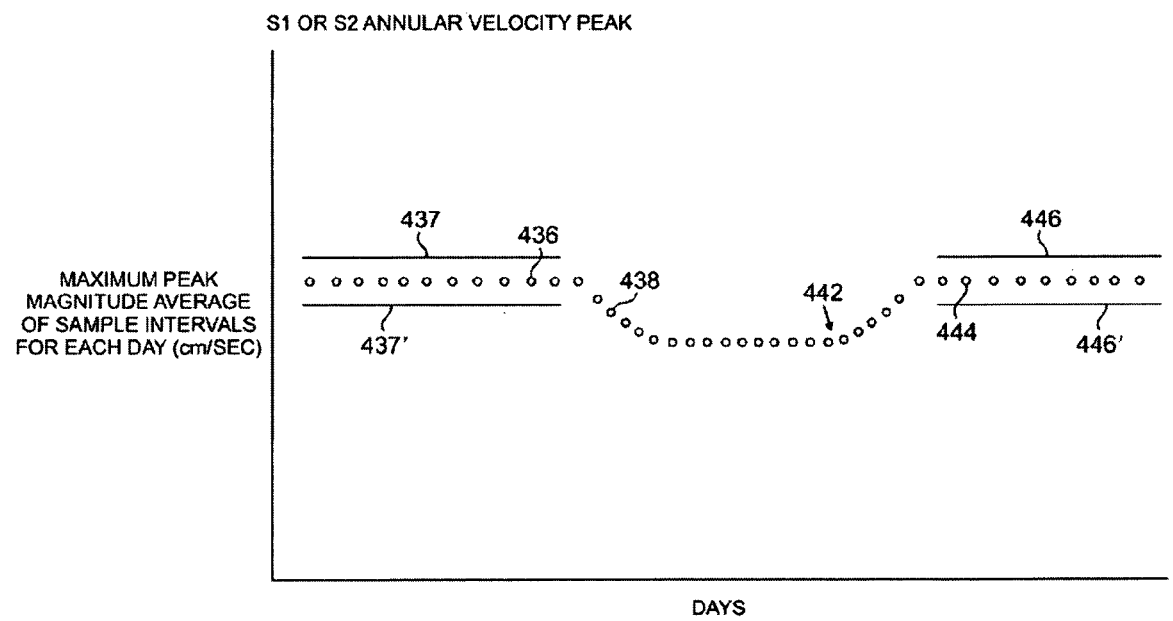
FIG. 18 shows a representation of long-term monitoring and therapy optimization.

For example, referring to FIG. 18, which shows a representation of long-term monitoring and therapy optimization, a patient is seen with a baseline level of maximum peak magnitude of the average of daily sample intervals of S1 or S2 annular velocities (line 436, with a standard error of mean (SEM) of daily average peak data 437 and 437'). Decline 438 may be seen, which corresponds to a decline in contractility, e.g., of the S1 peak. The decline may be defined in various ways, such as by a one or two SEM deviation from the baseline. A therapeutic intervention at 442 is shown, which is done to improve contractility. A new baseline is then evident at 444, with SEM bars at 446 and 446'.

These trends may also indicate when additional interventions are warranted such as cardiac surgery, endovascular revascularization, or CRT. It may be noted that these peaks have been characterized with tissue Doppler imaging at the posterio-lateral edge of the mitral valve annulus in a single plane. An epicardial acceleration sensor in the same region, that is recording acceleration in 1, 2 or 3 axes, may produce a somewhat different velocity curve. However, it is believed that the curve can be analyzed in a manner analogous or similar to that discussed below to provide useful information to the physician.

The S1 peak can be used to assess myocardial contractility with a higher peak indicating improved contractility and a lower peak indicating reduced contractility. A main goal of heart failure therapy is to improve myocardial contractility. Contractility can be improved with CRT therapy and pharmacologic therapy. The slope of this peak may provide similar information.

The S2 peak can be used to assess afterload, which is a measure of the resistance the heart must pump against as it circulates blood to the body. It is the goal of heart failure therapy to reduce afterload, primarily with the use of pharmacologic agents. Increases in the S2 peak represents increases in afterload, and decreases in the S2 peak represents reductions in afterload. Alternatively, integrating the area under the S2 peak may provide information on the afterload. The S2 peak also correlates with ejection fraction and rate of pressure change (dP/dt).

The E and A peaks can be used to assess cardiac compliance and patient volume status. In heart failure therapy, optimizing the patient's volume status and its effect on left heart pressure is important. Cardiomyopathy patients have a tendency to retain water and can become volume overloaded. When this occurs, the function of the heart deteriorates and symptoms such as pulmonary congestion occur. Diuretic drugs such as Lasix are commonly used to reduce water retention. Monitoring of the E and A peaks and slopes, and integrating the area under the curve, can provide information on volume status. In addition, the relationship of the E and A peaks (E/A) is indicative of ventricular compliance. Ventricular compliance can change with ischemic events and can be reduced with long-term elevated afterload. Beta-blocker therapy can affect compliance in cardiomyopathy patients and therefore may be monitored with the E and A peak data.

Figure 11:
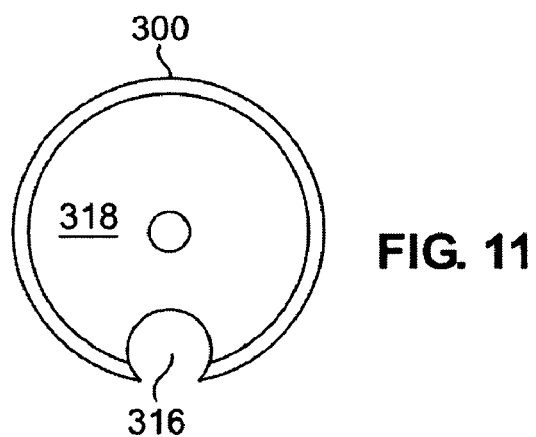
FIG. 11 shows a cross-sectional view of the lead of FIG. 10.
Figure 12:
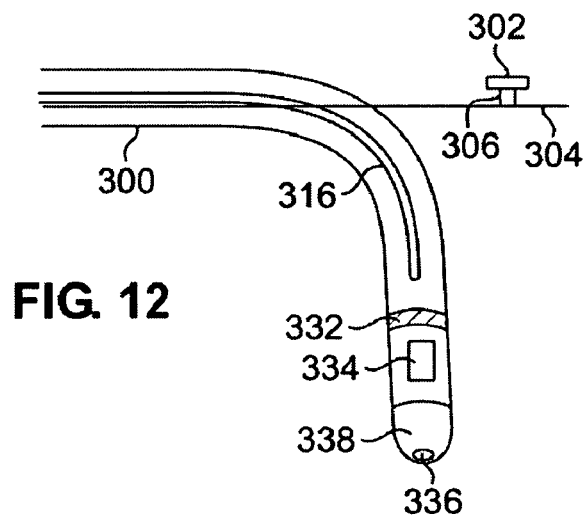
FIG. 12 shows the lead of FIG. 10 in a bent position, showing in particular the extension of the sensor.
Figure 13:
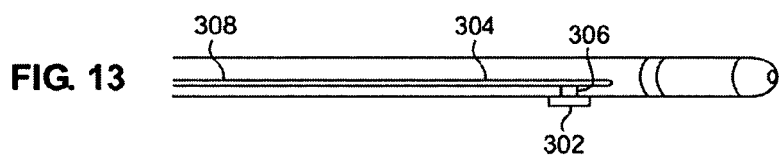
FIG. 13 shows an implantable LV lead with a sensor disposed on the outside of the LV lead.
Figure 14:
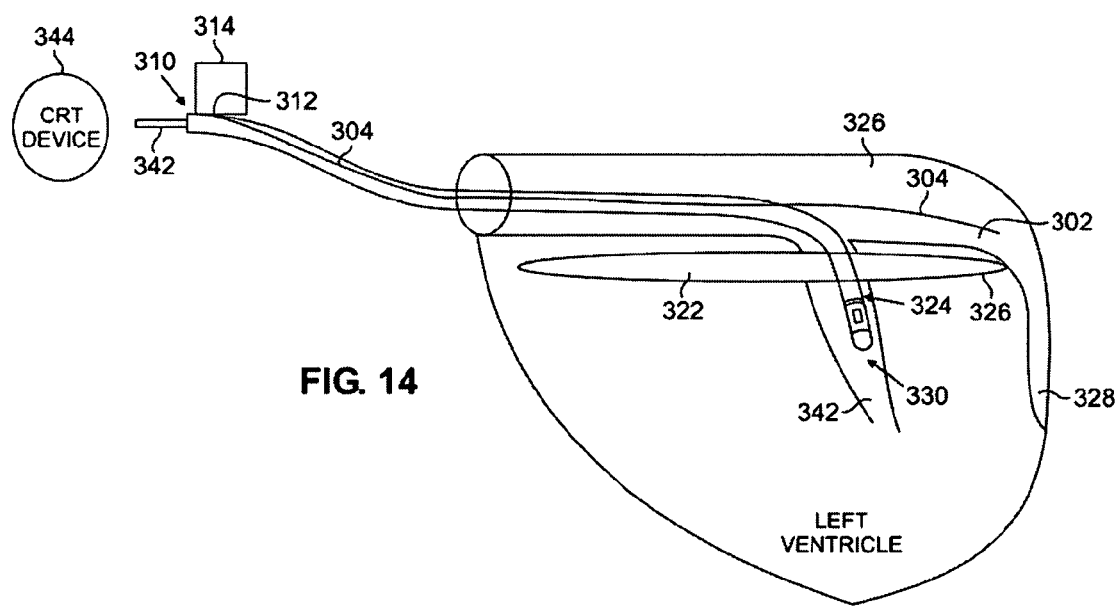
FIG. 14 shows the lead of FIG. 13 when positioned partially in the coronary sinus.

The A peak which represents atrial contraction can also be used to optimize atrioventricular timing in a patient with CRT therapy. AV synchrony optimizes preloading of the heart and improves pumping performance in part via the Frank Starling mechanism. Ideally, ventricular contraction occurs at the completion of atrial contraction, which produces optimal preloading of the ventricle. The end of atrial contraction and ventricular filling can be determined at the point at which the ventricular velocity crosses the abscissa after the peak of the A wave (FIG. 11). Subsequently, ventricular pacing signals can be triggered at this point.

Other measures of LV function can also be obtained by analyzing the time intervals of different phases of the cardiac cycle. Several time interval measures include the isovolumic contraction, ejection phase, isovolumic relaxation and LV filling time. Time intervals can be estimated from the acceleration, velocity, and distance data. The start of a time interval may be identified as an acceleration amplitude above a certain threshold (e.g., +/−milli Gs) and the end of an interval may be indicated by the dipping of the acceleration amplitude below a threshold value. Also, the number of zero crossings may also be used to estimate time intervals. A reduction in the isovolumic contraction or relaxation time interval would be indicative of a favorable response. Increase in the ejection phase time interval, e.g., QRS to aortic or pulmonic valve closure, and the filling time interval, would also be indicative of a favorable response.

Figure 21:
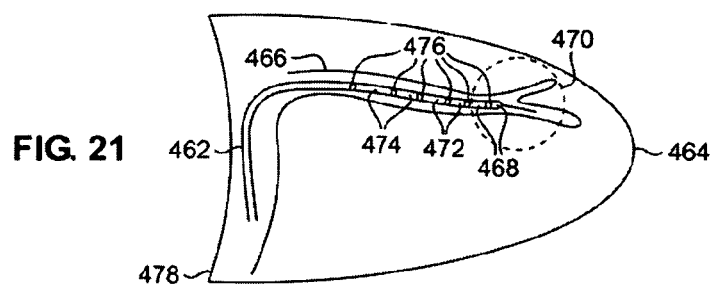
FIG. 21 shows positioning of a catheter employing multiple sensor pairs in the LV vein.

The myocardial performance index (MPI) is a measure of systolic and diastolic function that is a good predictor and monitoring indicator for heart failure. The index is calculated as the isovolumic contraction time plus the isovolumic relaxation time divided by the ejection phase time (FIGS. 18 and 21). A reduction in the value of the MPI is indicative of better LV function. The MPI may be assessed using an acceleration sensor by measuring the intervals as described above. In addition it may be assessed by monitoring mitral valve opening and closing from the coronary sinus or great cardiac vein and measuring the ejection phase due to LV shortening. Thus the time interval during systole between mitral valve closure and mitral valve opening minus the time interval of LV shortening divided by the time interval of LV shortening is indicative of the MPI.

Longitudinal displacement of the mitral annulus inferiorly during systole and superiorly during diastole is also a good measure of LV function. Thus a sensor in the coronary sinus or proximal the great cardiac vein with at least one axis oriented longitudinally will measure the acceleration of the annular region in the inferior and superior directions. From this, velocity and distance can be calculated through integration. The peak acceleration, peak velocity, and distance traveled by the annular region during systole are indicative of performance with higher values indicating better function. Similarly the velocity and peak acceleration during diastole as well as the distance traveled is a measure of LV performance with higher values indicating better function. The clockwise or counterclockwise rotation of the basal and annular region can be measured in the coronary sinus with an acceleration sensor oriented horizontally. Again, higher values of acceleration, velocity, and rotation are indicative of LV performance. Narrowing and widening anteriorly/posterialy and medial/laterally of the mitral annulus is also indicative of LV function. An acceleration sensor oriented radially to the heart in the coronary sinus or proximal the great cardiac vein could assess this motion with higher values indicative of better function. A 3-axis sensor could measure all axes of motion of the mitral annulus: longitudinal, radial, and rotational, for complete characterization of LV function from the coronary sinus. This would be useful for long term monitoring, identifying, and optimizing LV pacing regions during CRT lead placement as described below.

Figure 1B:
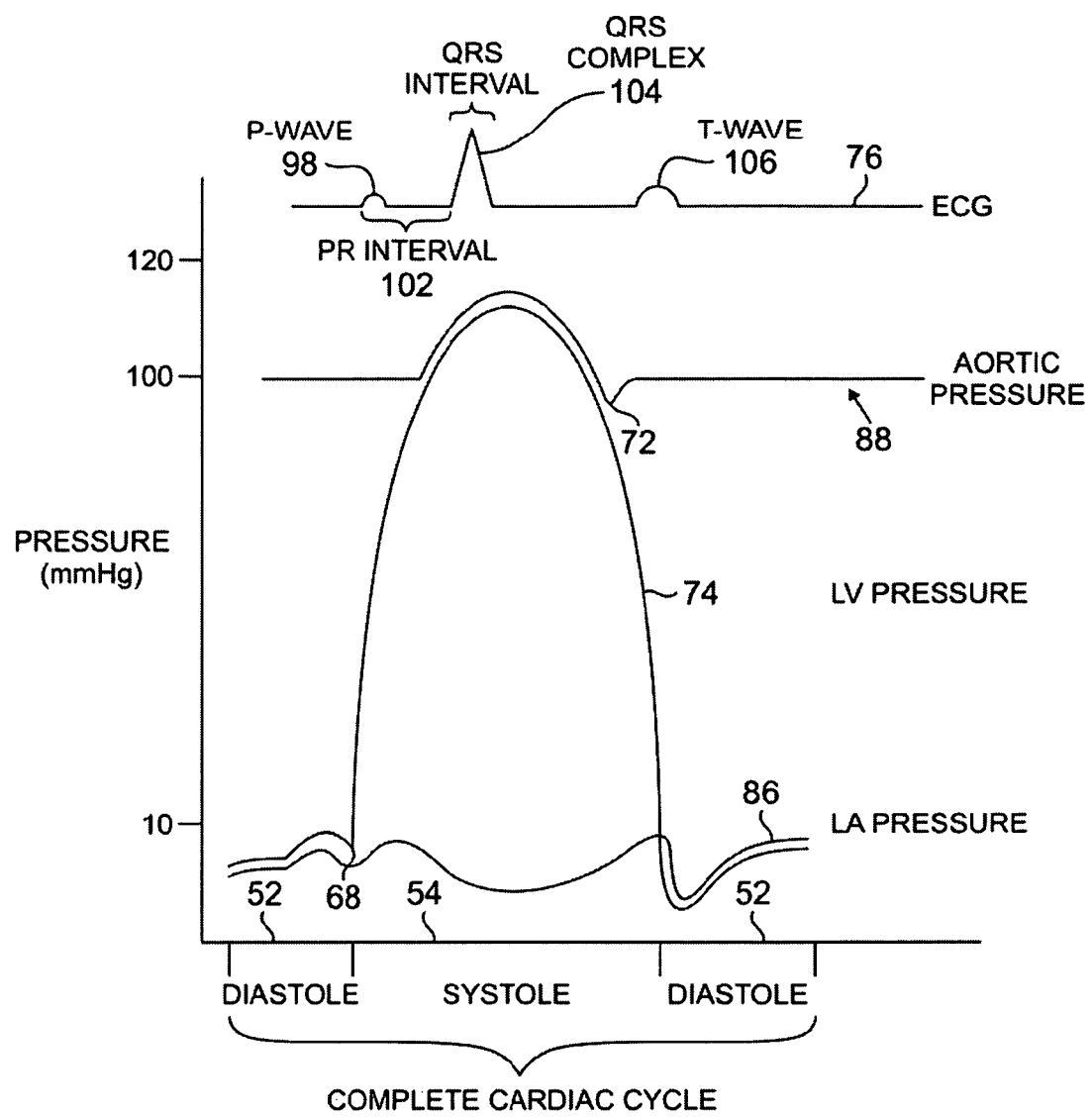
Figure 19:
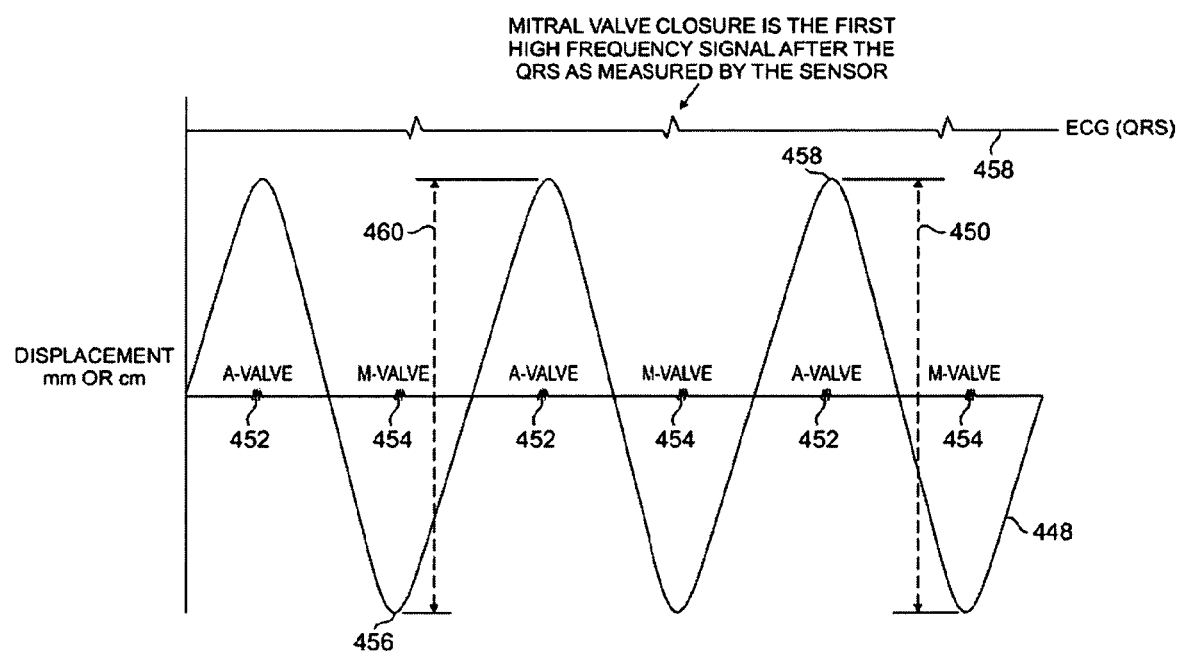
FIG. 19 shows the orientation of systolic and diastolic displacement as well as measurement of the displacement length.

Referring to FIG. 19, in which displacement, in, e.g., cm or mm, is shown as the ordinate, low frequency (1 to 10 Hz or less than 20 Hz) acceleration sensing associated with LV displacement and its respective integration of velocity and distance may appear as a semi-sinusoidal wave (curve 448) of positive and negative deflections with a frequency as a function of the heart rate. The orientation of the sensor axes determines if longitudinal displacement is a positive deflection or a negative deflection. By convention, longitudinal shortening is usually displayed as a negative or downward-moving deflection and lengthening as a positive or upward-moving deflection. If the orientation of the sensor is not known and cannot be determined easily, information recorded by the sensor may not allow the physician to distinguish systolic shortening from diastolic lengthening. Orientation can be determined by synchronizing the low frequency sensor data with the high frequency data or the QRS (see curve 458 and points 454, which signify mid-frequency (20-150 Hz) valve closure signals. Isovolumic contraction and relaxation signals occur with a similar mid-frequency.). Thus, the start of systole and shortening can be determined as the deflection that occurs after isovolumetric contraction, mitral valve closure, or alternatively the QRS. The double integration of the peak amplitude of the sensor data after mitral valve closure or isovolumic contraction or QRS is representative of peak longitudinal shortening. The same rationale can be applied to orienting longitudinal lengthening using isovolumic relaxation or the aortic valve closure sensor data or the T-wave (see FIG. 1B) as the reference point. Isovolumic contraction or relaxation or mitral or aortic valve closure can have distinctive vibrational signals detected by higher frequency sensing, allowing the same to be distinguished. However, mitral valve closure can be determined by comparing the sensor signal to the ECG, whereas the mitral valve signal will be the first signal detected after the QRS. The microprocessor can be programmed to display the shortening and lengthening according to convention.

To accurately measure the length or magnitude of ventricular deformation, peak velocities, or peak accelerations, during systole (or even diastole) along the radial or longitudinal axes, a zero reference point is preferably ascertained. This can be seen in FIG. 19 as point 456, for the zero point systolic deformation for length measurement, which also represents the peak diastolic length. A different peak 458 represents the zero point diastolic displacement, which is also the peak systolic shortening. As the sensor devices are maneuvered in the patient or as a patient moves, the tilt of the sensor with respect to gravity, i.e., the angle versus the gravity vector, will change. This sensor output due to the tilt signal must be accounted for or offset to accurately measure peak amplitudes and distance of shortening. For mechanical mapping (see below), the magnitude of shortening, or peak velocities or peak acceleration, could be assessed and regions that are activated earlier and have a greater magnitude of shortening would be selected for long-term CRT pacing. Also, the optimal pacing capture threshold could be determined by applying pacing signals of increasing strength (millivolts). Monitoring the magnitude of the deformation and correlating this with the pacing signal strength optimizes the pacing threshold (see FIG. 26. Further, the qualitative assessment of lengthening or shortening is facilitated by having a zero point.

Referring again to FIG. 19, valve closure or isovolumic contraction or relaxation can provide the zero-offset reference point. Alternatively, the onset of the QRS can be used to determine the zero point. Hence, length of systolic shortening 460 is measured as the peak amplitude of the double integration of acceleration data sensed after isovolumic contraction and/or mitral valve closure or QRS onset. Similarly, the length of diastolic lengthening 450 is measured as the peak amplitude of the double integration of the acceleration data after isovolumic relaxation and/or aortic valve closure, i.e., the diastolic zero point. The tilt reading, or tilt offset, of the sensor can also be accounted for by using the QRS onset, mitral valve closure, or aortic valve closure from the signals measured. Thus, the capacitive signal sensed by the sensor at the above reference points can be subtracted out from subsequent signals being measured to detect LV lengthening and shortening. Accurate assessment of diastolic lengthening as noted above allows the physician to monitor the filling and the dilated state of the left ventricle.

Trends of increasing diastolic lengthening are indicative of volume overload, while reduction in diastolic lengthening represents improvements due to volume unloading. This data may be trended in an implantable device according to an embodiment of the current invention and is useful in the mapping procedure to assess the effect of pacing the target region which may then shows a reduction in peak diastolic lengthening due to improved pumping and volume unloading.

Figure 20A:
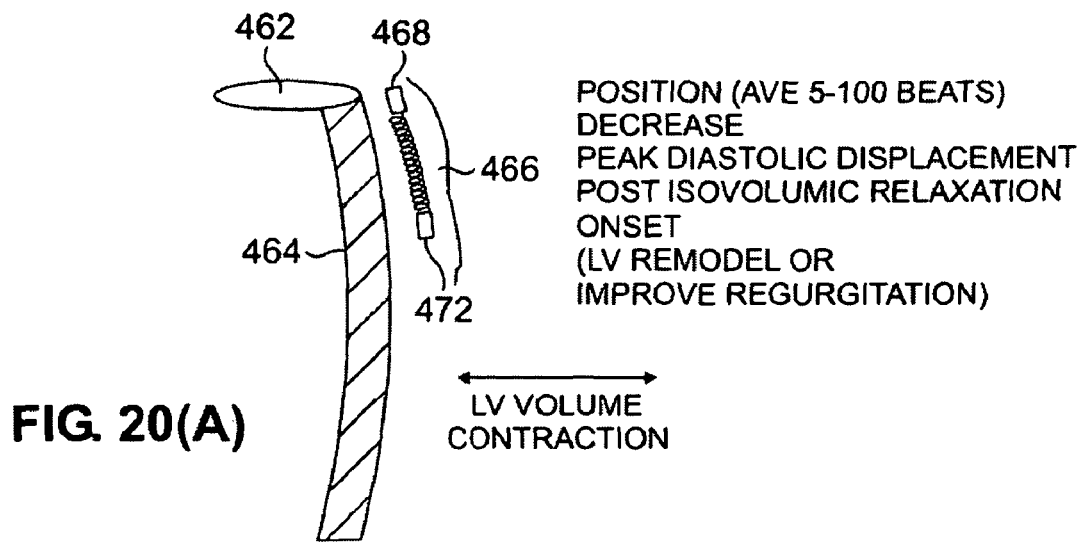
FIG. 20(A)-(C) show an assessment of LV size for acute response to CRT and long-term monitoring.
Figure 20B:
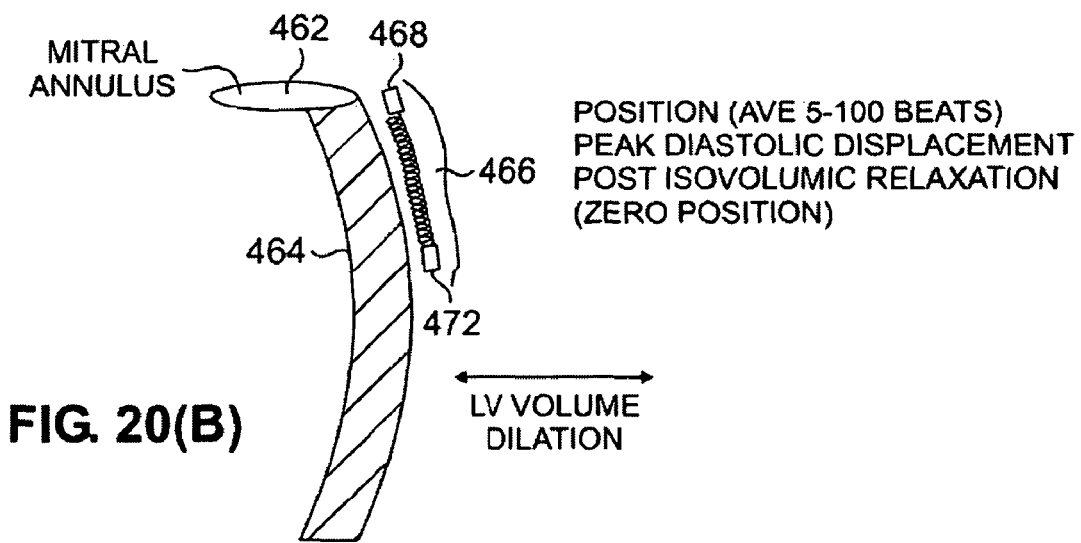
Figure 20C:
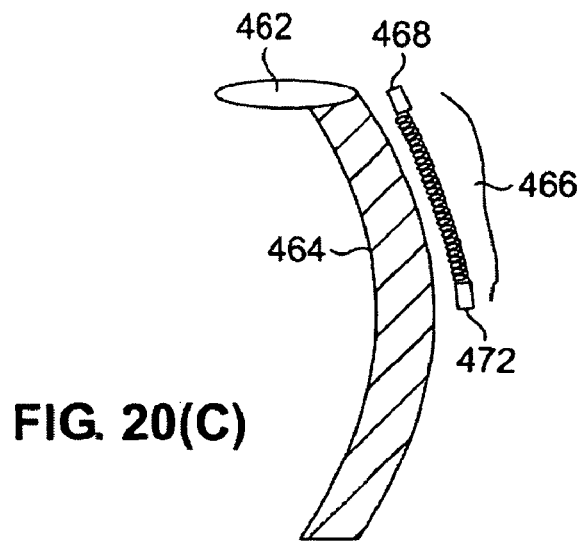

Referring to FIG. 20(A)-(C), assessment of LV size for acute response to CRT and long-term management is shown. As heart patients regain fluid the LV can become enlarged. Benefits are seen as reduced LV volumes. By having a sensor on the lateral wall, the relative movement as the LV is enlarged could be monitored. Sensors also allow the establishment of a reference point.

FIG. 20(A)-(B) shows mitral annulus 462, LV wall 464, and cardiac vein 466 in which is situated high frequence sensor 468 and low frequency sensor 472. FIG. 20(B) shows the position of the sensor on the heart at the end of the filling phase (post isovolumic relaxation). If the heart improves, the sensor moves inward to reflect the smaller size (FIG. 20(A)). If the heart enlarges the sensor moves outward (FIG. 20(C)). Thus, used in this was, embodiments of the invention give a measure of diastolic filling or dilation.

Mitral regurgitation can be caused by LV dilation and functional decline, which worsens the symptoms of heart failure and is associated with faster deterioration of the heart. CRT can improve mitral regurgitation. Mitral regurgitation can cause higher frequency (>200 Hz) motion that can be sensed at the mitral valve annulus from the LV vasculature with the acceleration sensor. The amplitude of the acceleration signal and duration relative to the ejection phase may be good indices to measure for improvement. A reduction in amplitude and duration is indicative of improvement. A change in the frequency may also be indicative of improvement. The vibrational motion associated with isovolumic contraction may be indicative of the contractility of the heart. Increases in the peak of this signal may indicate better contractile function.

For trend monitoring (e.g., with an IAD), acceleration data is sampled at regular intervals during the day, termed the "interval period", and this data is averaged. Peak amplitudes can be plotted as the ordinate with the monitored time interval (e.g., days, weeks, or months) as the abscissa (See FIG. 18). Data points may indicate the average amplitude of the peaks from the interval samples. Statistical analysis of these trends can identify changes from baseline function that may warrant an intervention.

Disposable and Mapping Acceleration Sensor Devices

LV motion may be useful for identifying target pacing regions for CRT.

Target pacing regions may be identified by how late the region of the LV starts shortening relative to a reference point such as onset of systole or end of systole (See, e.g., FIGS. 21-24).

Referring to FIG. 21, a catheter 462, which may perform mapping, is shown within the posterior LV or lateral LV 464, and in particular within the LV vein 466. The catheter 462 includes a sensor pair 468, a sensor pair 472, and a sensor pair 474. The catheter 462 also includes electrodes 476. Area 470 indicates the segment of late displacement. The mitral annulus is shown at position 478.

Figure 22:
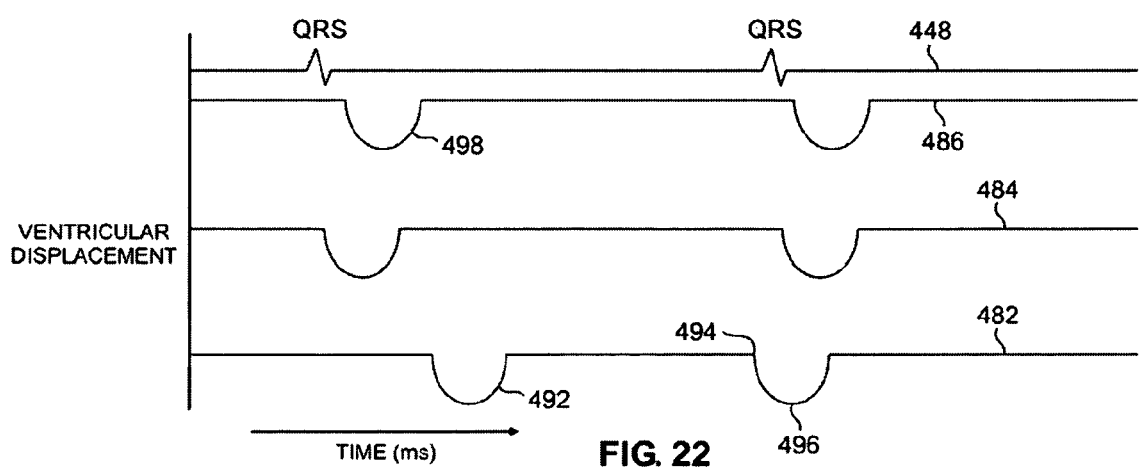
FIG. 22 shows a graph indicating location of a mapping catheter as well as sensors in the LV.

FIG. 22 shows displacement curves which identify a late shortening segment in the posterior region. Pacing of this region causes earlier displacement and synchrony with other segments. The abscissa represent time in milliseconds. The ordinate represents ventricular displacement, but similar curves may be drawn representing velocity or strain rate. The measurement from sensor pair 468 is shown by curve 482; the measurement from sensor pair 472 is shown by curve 484; and the measurement from sensor pair 474 is shown by curve 486. An ECG is shown as curve 488, with representative QRS waveforms.

Along curve 482, feature 492 represents late shortening. Feature 494 represents a pacing signal from one of electrodes 476, in particular an electrode adjacent sensor pair 468. Feature 496 depicts earlier shortening of the late segment and optimized ventricular synchrony. Along curve 486, the baseline is chosen as the sensor position at QRS onset, or the onset of isovolumic contraction, or the end of the A-wave. The negative deflection shown in feature 498 reflects the shortening of the LV.

Uncoordinated LV contraction due to delayed regional shortening reduces the efficiency and effectiveness of blood pumping and hence delayed regions are targets for pacing. Myocardial shortening that occurs after aortic valve closure, i.e., post-systolic, does not contribute to the ejection of blood and may exacerbate pathologic conditions such as mitral regurgitation and hence these regions are also targets for pacing. Both longitudinal and radial shortening may be delayed. Late onset shortening or post-systolic shortening may be best measured at low frequency acceleration signals related to displacement. The integration of the acceleration signal to a velocity or distance may also smooth out the signal and make it easier for the physician to interpret. A reference point for delayed systolic shortening and post-systolic shortening may be the QRS onset and T-wave, respectively.

Figure 23:
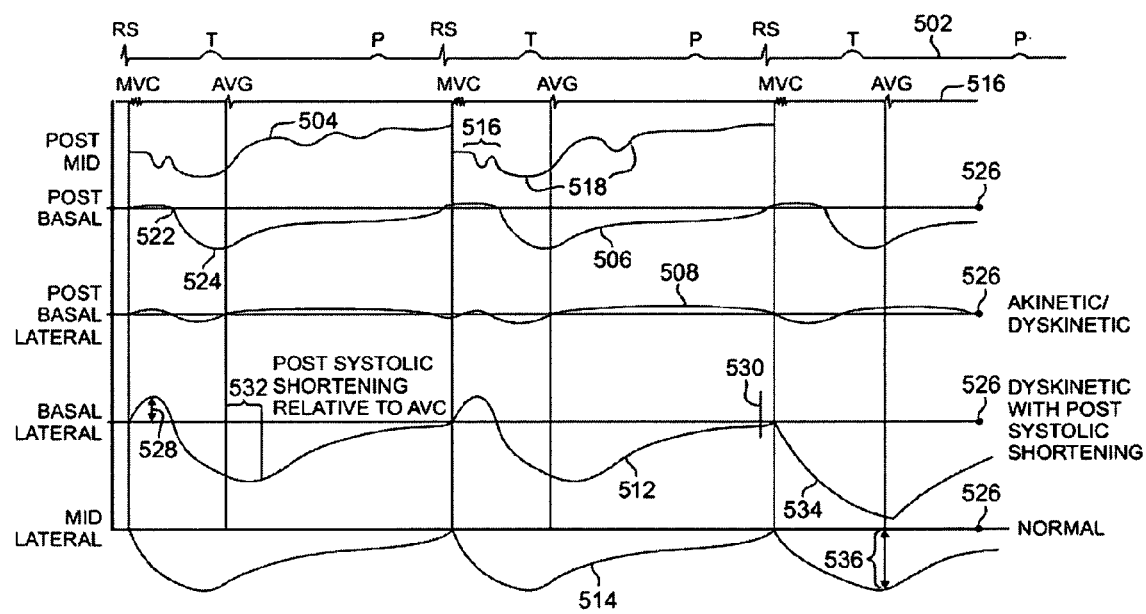
FIG. 23 shows differing shortening or displacement patterns in various regions of the heart.

FIG. 23, shows various shortenings or displacement patterns in various regions that indicate dyssynchronous LV signals and probable responders to CRT. Delayed onset shortenings and post-systolic shortenings are target pacing regions.

Curve 502 represents an ECG with the Q, RS, and T waveforms shown. Curve 516, which is straight, shows sound waveforms of the MVC and AVC. Curve 504 represents a post-mid-segment measurement. Curve 506 represents a post-basal measurement. Curve 508 represents a post-basal-lateral measurement. Curve 512 represents a basal-lateral measurement. Curve 514 represents a mid-lateral measurement. Various features of these curves will now be described. In all the curves, points 526 represent the zero point position of the sensor at either QRS onset, MVC, or AVC. Also in all curves, the target pacing region was the basal lateral, and the example shows delayed onset shortening, early systolic lengthening, and post-systolic shortening.

Referring to curve 504 in FIG. 23, features 516 represent a shortening and lengthening dyssynchronous pattern. Features 518 show a dysssynchronous contraction pattern. Referring to curve 506, which shows a delayed hypokinetic response, feature 522 reveals a delayed onset motion relative to the QRS or MVC. Feature 524 reveals a reduced peak displacement or shortening hypokinesis. Curve 508 shows an akinetic or dyskinetic response. Curve 526 shows a dyskinetic response with post-systolic shortening. This curve also shows early systolic lengthening at feature 528, post-systolic shortening relative to AVC at feature 532, and normalized displacement or shortening at feature 534 following pacing spike 530. Curve 514 shows a normal heart rhythm with peak shortening at feature 536.

Alternatively, vibrational components of the LV cycle may be used as reference points. Thus a reference point for delayed systolic shortening within systole may be the vibrational motion associated with isovolumic contraction or mitral valve closure. Similarly, vibrational motion associated with isovolumic relaxation or aortic valve closure may serve as reference points for post-systolic shortening. These reference points occur in the mid-frequency range (e.g., 20 Hz-150 Hz), while the displacement motion occurs at the low frequency range (e.g., <10 Hz). These signals can thus be separated out by appropriate filtering. Post systolic shortening more than about 20-50 milliseconds or greater than 20% of the total regional shortening after aortic valve closure could be a target pacing region. Other targets are dyskinetic regions that have periods of lengthening during early systole followed by shortening deformation, or akinetic regions that have lengthening throughout systole (FIG. 16).

LV motion, both regional and global, can be used to characterize indices of LV function in response to pacing. Thus, identification of a region of late or post-systolic shortening may be performed, and/or a pacing electrode can be positioned in the region and paced at a threshold that ensures tissue capture.

FIG. 17 shows a mapping method, for the LV, for CRT LV lead placement. A first step is to place the guide catheter in the coronary sinus (step 538). A next step is to insert the catheter with the acceleration sensor into the guide catheter and into the coronary sinus (step 542). A next step, which is optional, is to measure the onset of displacement motion, e.g., velocity or distance, relative to the onset of systole, as determined via QRS or isovolumic contraction (step 544). Step 544 may be performed by moving the catheter in the coronary sinus and great cardiac vein or tributary veins, e.g., in a septal to lateral manner. A next step is to insert the pacing guide wire through the guide wire lumen of the acceleration sensing catheter and then into the tributary veins of the coronary sinus and the great cardiac vein (step 546), e.g., the basal, mid, and apical regions. A next step is to pace the region in the tributary vein (step 548). A next step is to measure the acceleration signal characteristic of LV function, e.g., QRS to AVC; the myocardia performance index (MPI); or mitral regurgitation (step 552), for which the peak acceleration is at the isovolumic contraction. The final step is to insert the LV lead over the guidewire to the target region, i.e., the region with improved LV function (step 554).

Figure 25:
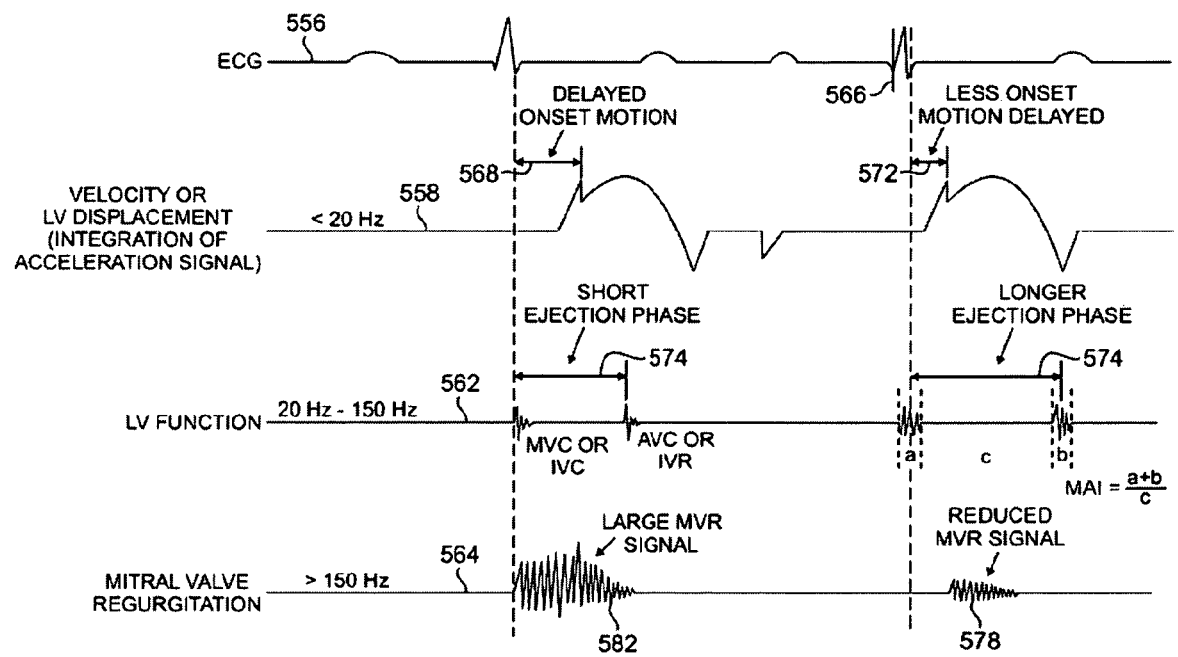
FIG. 25 shows myocardial motion mapping, display output, and target pacing identification.
Figure 33:
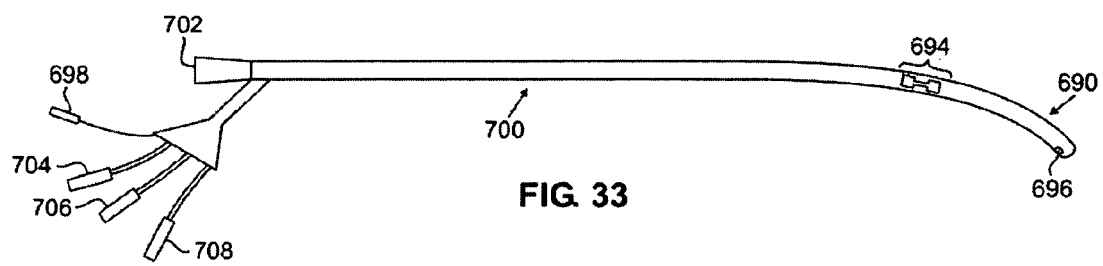
FIG. 33 shows a system that may employ the guide wire of FIG. 31 or the guide catheter of FIG. 32.

Referring to FIGS. 25 and 33, which shows myocardial motion mapping, display output, and target pacing identification through a roving pace guidewire, changes or variables indicative of a favorable LV functional response may be sensed at the low, mid, and high frequency ranges. In the figure, "MVR" refers to mitral valve regurgitation, "IVC" refers to isovolumic contraction, and "IVR" refers to isovolumic relaxation. The top curve is ECG 556, curve 558 shows the velocity or LV displacement, obtained by integrating the acceleration signal, curve 562 shows LV function, and curve 562 shows the sounds of mitral valve regurgitation.

ECG 556 shows the QRS and T waves along with a pacing spike 566 which is delivered in the LV vein region. Examination of curve 558 shows a delayed onset motion 568 but a lessened delayed onset motion 572 following the pacing spike. Curve 562 shows a value of ejection phase 574, as measured by the time between the MVC or IVC and the AVC or IVR, and then a longer ejection phase 576. Here the MPI can be seen to be MPI=(a+b)/c. Finally, curve 564 shows a reduced MVR signal 578 as compared to the pre-pacing MVR signal 582.

As shown above, low frequency changes or variables indicative of a favorable response to pacing include but are not limited to: either temporally earlier or more synchronous shortening of the paced region; increases in longitudinal or radial displacement of the mitral valve annular region; increases in peak acceleration or velocity of longitudinal or radial displacement of the mitral annular region (S1 or S2 peak). The change in radial and longitudinal shortening may reflect the ejection fraction, a variable correlated with outcome in heart failure. The position of the LV wall as determined by the sensor may determine the effects of pacing on LV volume (See FIG. 20). Mid frequency indices or variables associated with improved LV function include but are not limited to: steepening of the slope or an increase in the peak amplitude of the isovolumic contraction phase; shortening of the isovolumic contraction time interval; shortening in the isovolumic relaxation time interval; increases in the LV filling time relative to the cardiac cycle length; increases in the time of aortic valve closure or mitral valve opening from QRS onset divided by the cardiac cycle length; increases in the systolic ejection phase time interval; increases in the time from QRS onset to aortic or pulmonic valve closure; and increases in the time from QRS onset to aortic or pulmonic valve closure divided by the cardiac cycle length. Changes in LV function indicative of a favorable response to pacing at the high frequency range would be a reduction in mitral valve regurgitation amplitude and duration as well as a frequency change. Lastly, the myocardial performance index may be also utilized as a measure of LV functional response and the same may be determined from mid-frequency signals or a combination of mid- and low-frequency signals.

Figure 26:
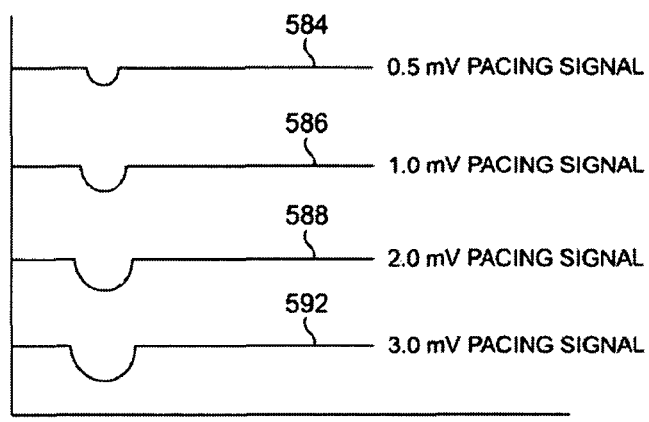
FIG. 26 shows optimization of the pacing capture threshold.

Pacing of certain regions may not produce improvements in LV function. Ischemic regions may not respond to pacing or may contract poorly due to the presence of non-contractile tissue and may therefore be avoided. It should also be noted that the displacement and the related strain rate can be used to diagnose areas of ischemia, which may also be useful in optimizing CRT, such as by avoiding the pacing of these regions. As an example, regions where shortening is delayed or disappears under stress conditions, e.g., increased oxygen demand, such as dobutamine infusion, are likely due to ischemic blood flow. Other factors, such as the ability to electrically couple to the region, may affect pacing. Pacing capture thresholds must be determined, which could occur by increasing the pacing stimulus and measuring the displacement, which is shown in FIG. 26. In particular, curves 584-592 represent pacing signals from 0.5 mV to 3.0 mV. Curve 584 shows a small shortening, curve 586 shows more, and curve 588 shows still more. However, no difference in shortening is seen between curve 588 and curve 592, thus the optimal capture threshold can be determined to be 2.0 mV. Interval timing such as simultaneous ventricular pacing, RV first pacing, or LV first pacing, may also need to be optimized to produce the desired response.

LV motion sensing with an acceleration sensor primarily at low frequency may allow the identification of candidates for CRT. Many patients with a low ejection fraction and history of ischemic heart disease undergo the implantation of a defibrillator. During the defibrillator placement, a candidate for CRT could be identified and an LV lead placed, thus preventing the exposure of the patient to two separate procedures.

One way to assess candidates for CRT is by assessing contractile reserve. The presence of shortening during diastole is indicative of contractile reserve. The difference in peak ejection velocity or shortening or the start of motion or shortening in any two regions, e.g., the septal to posterior region or the posterior to lateral region, is indicative of dyssynchrony that may respond to therapy. These differences may be based on the time from onset of systole for each region or may be the direct difference between two regions. Thus, a difference in peak velocity from the septal to posterior wall of greater than 50-100 ms may indicate a target pacing region of the posterior wall. Septal motion could be detected by a sensor located in the RA/RV or near the opening to the coronary sinus or near the posterior interventricular vein branch. Specific displacement patterns, such as both shortening and lengthening, that occur between QRS onset and aortic valve closure (FIG. 23), are indicative of dyssynchrony. These delays in regional shortening, post-systolic shortening, and dyssynchronous contraction patterns, may be present regardless of QRS duration and hence can be used to identify candidates and responders even if the QRS is normal or only modestly widened.

Figure 27:
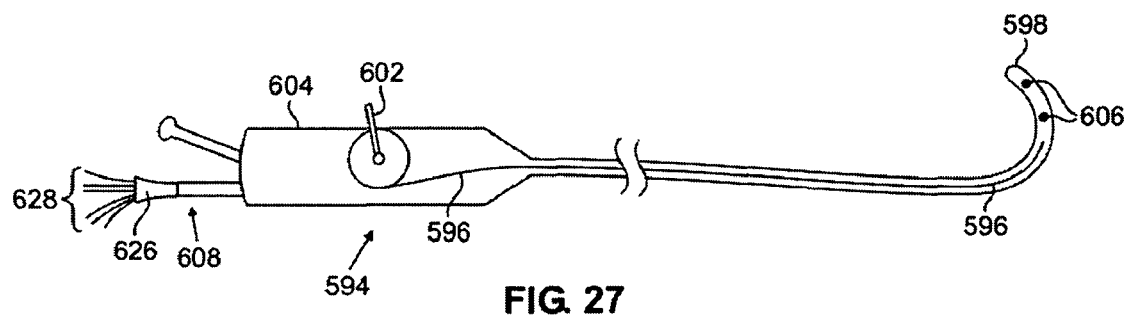
FIG. 27 shows a multi-sensor multi-electrode mtion mapping catheter system.
Figure 28:
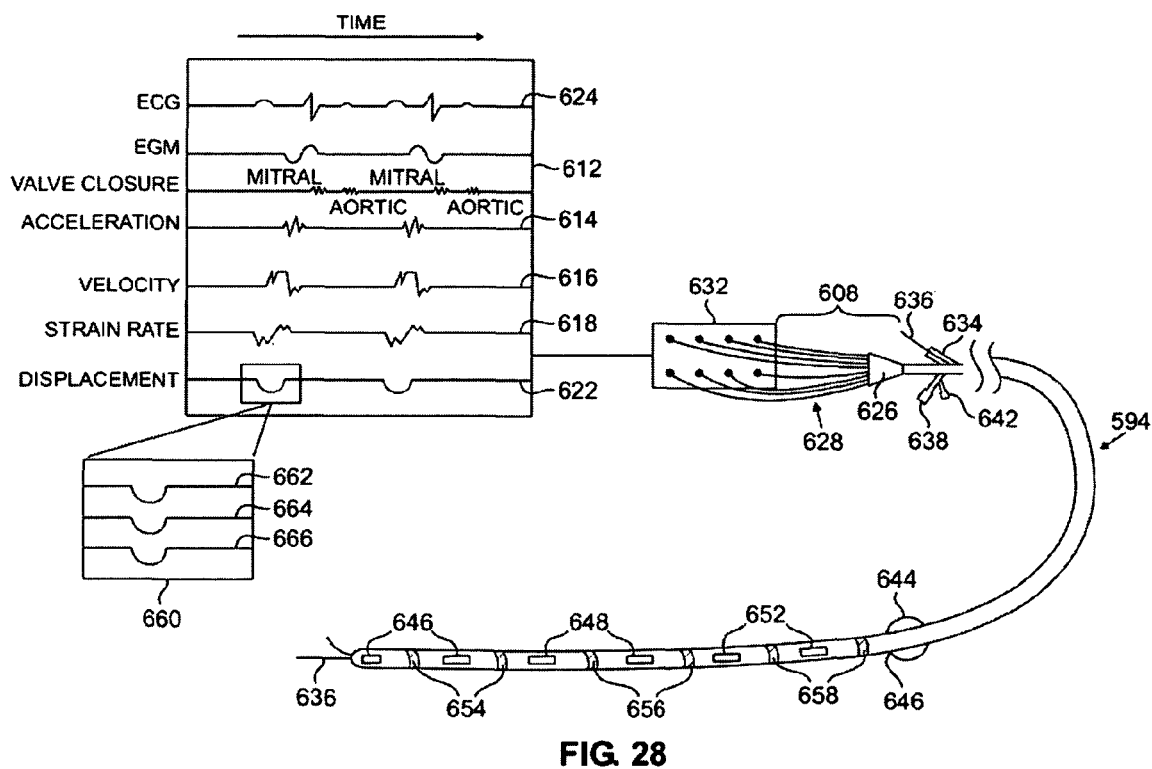
FIG. 28 shows a more detailed view of the system of FIG. 27.

To accomplish target pacing region identification, characterization, pacing optimization, and to identify candidates for CRT as described above, a myocardial motion mapping system may be employed (FIGS. 25, 27 and 28). This system shows a multi-sensor, multi-electrode motion mapping catheter system 594. An acceleration sensing device, such as a catheter, LV lead, guidewire, guide catheter/catheter system, or a combination thereof, is used as a mapping device by positioning the device in various locations of the coronary sinus and LV vasculature (FIGS. 22 and 23). If desired, the acceleration sensing devices may be placed in the ventricular chambers, preferably the LV. If a single or two axis sensing is used, the catheter can be rotated until the optimal signal is detected. This may occur when at least one sensor is parallel to the axis of motion. Marker bands on the catheter could indicate the appropriate sensor orientation during the procedure or reference points as described previously could be used. Alternatively, 4-axis sensing could be employed using two dual axis sensors as described above. In this configuration, three of the four axes are used to measure acceleration in the x-, y-, and z-orientations for 3-axis sensing and the fourth channel may be used for sensing vibrational motion and valvular events or pathology. Alternatively, 6-axis sensing with three perpendicular dual axis sensors could be employed with three axes used to detect displacement motion and three axes used to detect vibrational motion. The acceleration sensing device could be guidewire directed or steerable, including tip deflection. Steerability is accomplished by having one-to-one, or as substantially close to this as possible, torqueability which can be accomplished with a braided catheter design. Tip deflection can be accomplished with wires 596 that run the length of the device and are affixed to the tip 598 (FIG. 27). A lever 602 in the handle 604 of the catheter pulls the deflection wires 596, producing deflection at the tip 598. Steerable deflection devices are familiar to those skilled in the art. One or more sensors 606 and pacing electrodes (see FIG. 28) may be located immediately adjacent to each other or the pacing electrode may be located between the sensors. The region of the sensor in the mapping catheter may be highly flexible as described above to ensure that the sensors move in concert with the myocardium. The catheter 594 may further be equipped with a connector 608 that includes a hub 626 and a plurality of connectors 628, which may include acceleration input connectors and electrode pacing connectors, that may connect to an microprocessor-based display system (see FIG. 28) including a manifold 632.

Referring to FIG. 28, the system 594 may further include a guidewire insertion port 634 for guidewire 636, an optional port for contrast injection 638 with an accompanying contrast port 646, an optional port for balloon inflation and deflation 642 coupled to an optional venogram balloon 644. Also included are, e.g., three sets of sensor pairs 646, 648, and 652, and three sets of electrodes 654, 656, and 658. The sensors may be, e.g., 5-10 mm apart.

Referring to FIG. 28, the mapping acceleration sensing device 594 may be directly connected to a microprocessor-controlled display 612 that presents motion signals as acceleration 614, velocity curves 616, strain rate curves 618, and displacement curves 622, or some combination of the three, with ECG data 624. The catheter and acceleration signal can also be input into a cardiac electrogram data acquisition system as may be already used by the physician. The acceleration signal may be displayed as a voltage, similar to the cardiac electrogram. The onset of motion signals may be easily displayed and compared to the surface ECG or intracardiac electrogram. Other reference points, as disclosed earlier, such as isovolumic contraction or valve closure, may also be displayed. (FIG. 25). The mitral valve regurgitation signal may further be displayed.

Also shown in FIG. 28 is close-up display 660, containing curves 662-666. These curves display displacement data corresponding to the three pairs of acceleration sensor data for mechanical mapping. In these figures, shortening is exhibited by a negative deflection.

Additionally, the mapping acceleration sensing device may be used to facilitate coronary sinus access and cannulation of LV vein branches that feed into the coronary sinus, necessary steps in the mapping process and LV lead implantation. One method to achieve access to the coronary sinus is conducted by dragging the mapping device from the AV node superiorly along the base of the RA, the interatrial septum, or the medial RA wall. When the device moves over or is near the coronary sinus ostium, the flow of blood from the ostium into the RA causes the device and/or tip to deflect or vibrate. The deflection or vibration may be sensed by the acceleration sensor. In addition, once the device is in the coronary sinus, it can be dragged or pushed along the inferior or lower border of the sinus. LV veins are detected by deflection or vibration by the sensor as it passes over the ostia, or branches, of the veins that drain into the coronary sinus. Alternatively, Doppler flow crystals and MEMs pressure sensors, and anemometry flow sensors may be used for coronary ostium identification and LV vein branches. These sensors may also be combined with the acceleration sensor.

Figure 29:
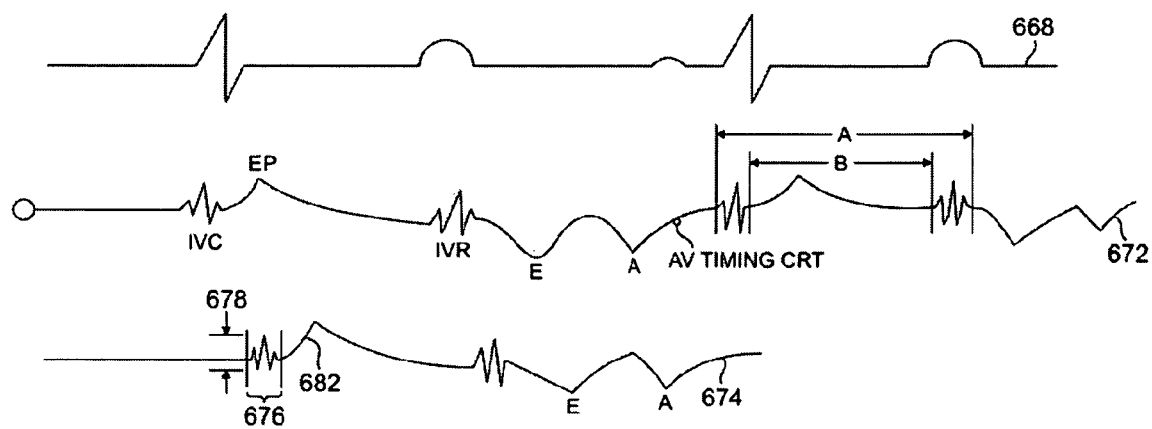
FIG. 29 shows acceleration signals used to identify regions of late deformation and for assessing various other variables related to performance such as MPI, IVC time interval, peak IVC height, etc.

In one embodiment, motion signals may be derived from serial, or various, combinations of the sensors or sensor pairs, at a known distance of separation, e.g., 5-15 mm, and may provide multiple velocity, displacement, and strain rate curves synched with a signal related to the start of systole such as single QRS or a contraction stimulus, or isovolumic contraction or mitral valve closure (FIGS. 23 and 28). Systole may also be induced by a separate pacing catheter conductively coupled to the RA or RV septum. Regions of late motion onset relative to the onset of systole, determined by the R wave of the ECG, septal activation on the EGM, or mitral valve closure, may be identified. Also, regions of post-systolic shortening relative to isovolumic relaxation or aortic valve closure or the t-wave may be identified. These late and post-systolic shortening regions may subsequently be paced by electrodes between the sensors that identified the late motion onset to elicit earlier activation. A new set of deformation curves may then be analyzed to confirm that the region of early activation pacing produces a more synchronous deformation. Further, the mid-frequency sensor measures the change in peak acceleration or velocity during the pacing of the identified target region, confirming a positive response to pacing (FIGS. 23 and 29). LV functional responses such as the myocardial performance index could also be measured during the test pacing (FIGS. 25 and 29).

Figure 30:
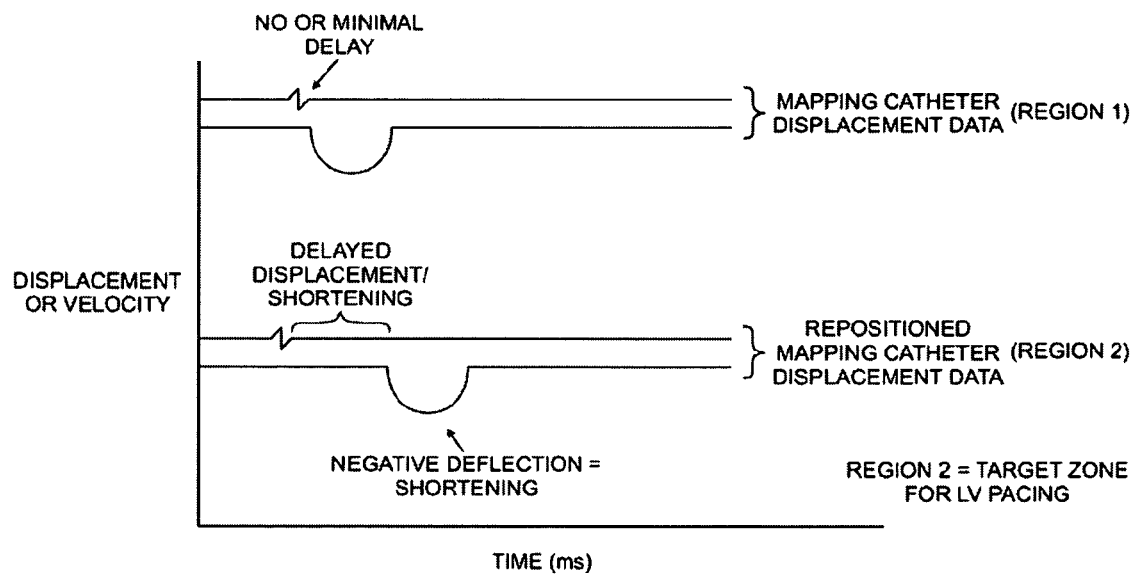
FIG. 30 shows an alternative mapping strategy involving multiple catheter repositionings.

Referring in more detail to FIG. 29, a chart is shown which may be used to identify regions of late deformation and for assessing various other variables related to performance. Curve 668 shows the ECG signal, curve 672 shows the acceleration signal, where the left-most point is the zero point established by the QRS, "EP" refers to the ejection phase, "E" refers to early diastolic filling, "A" refers to atrial contraction filling, time interval "A" measures the start of IVC to the end of IVR, and time interval "B" measures the time interval of the EP. MPI=(A−B)/B. Curve 674 shows the acceleration signal from region #1, showing in particular the IVC time interval 676 and the peak IVC signal 678, as well as the delayed mechanical shortening 682 in the target pacing region. Referring to FIG. 30, an alternative mapping strategy may also be employed in which a simplified catheter with only a 1, 1 pair sensor, i.e., perpendicular to each other, or 3 sensors, each perpendicular to each other, uniaxial, biaxial, or triaxial, is positioned in various LV and LV locations, e.g., septal to lateral in the coronary sinus and great cardiac vein). One sensor or sensor pair detects both the onset of systole or diastole, e.g., isovolumic contraction or relaxation; or aortic or mitral valve closure, and regional motion, or one of two sensors or one of two sensor pairs may be utilized to detect the same onset of systole or diastole and the other sensor or sensor pair detects the regional motion. Alternatively, 3 axes of a dual axis pair may be used for displacement sensing and the 4$^{th}$ axis may be used for vibration sensing. Alternatively, 3 axes of a 3-sensor device may be used for sensing displacement motion, and the other 3 axes may be used for sensing vibrational motion. No electrodes, one electrode, or two electrodes may be employed.

The regional motion from each location is recorded and stored and displayed. The motion at each location is compared against the QRS or endocardial pacing signal or the other systolic and diastolic reference points. The region of latest motion relative to the reference point is identified and the lead is positioned to the same anatomical location. It should also be noted that epicardial mapping may be performed during open chest or minimally invasive procedures using the same principles and sensors as above and appropriate device designs.

Figure 24:
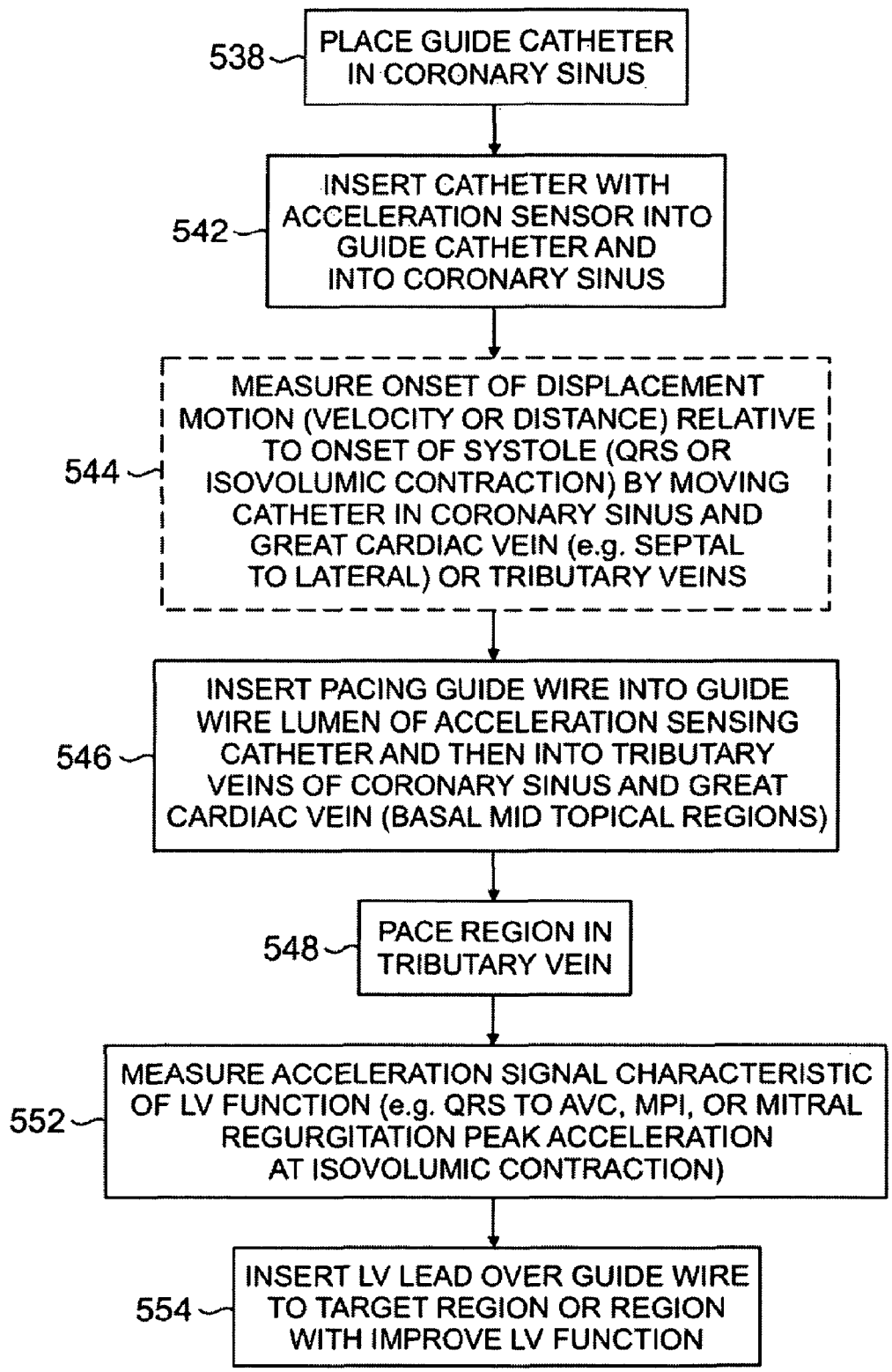
FIG. 24 shows a method for mapping the LV for CRT LV lead placement.
Figure 31:
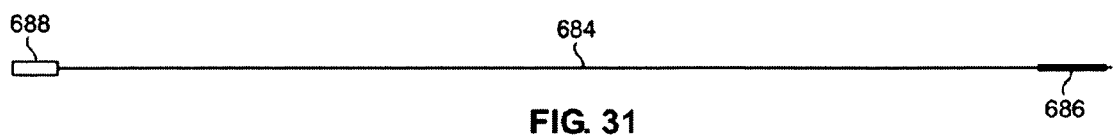
FIG. 31 shows a roving pacing guidewire device and acceleration sensing catheter for target pacing region identification as well as for characterizing the changes in LV function due to pacing.
Figure 32:
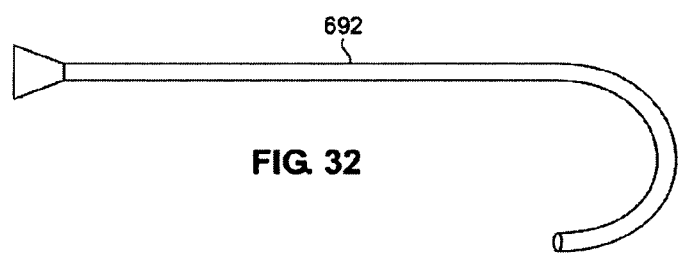
FIG. 32 shows a guide catheter that may be used with the system of FIG. 31.

In another mapping strategy, a roving electrode (e.g., a guidewire) can be positioned in various locations of the LV venous system and RV chamber and a test pacing stimulus applied to the myocardium. Referring to FIGS. 24 and 31, a guidewire 684 with an uninsulated region or electrode region 686 may be connected to a pulse generator via connector 688 and unipolar pacing may be performed. The guidewire may also have two uninsulated regions or two electrode regions for bipolar pacing. The LV functional effects of the test pace can be measured by an acceleration sensor or a dual axis sensor pair perpendicular to each other. The sensor or sensors may reside on a coronary sinus guide catheter 692 (see FIG. 32) or on a catheter 700 within the lumen within the coronary sinus guide catheter 692 (see FIG. 33). The catheter 700 may further have a pacing guidewire port 702 to accommodate guidewire 684.

For example, the sensors 694 may reside on catheter 690, and may be battery powered via battery 698. The sensors may number one, two, or three, each perpendicular to the others, and may have outputs corresponding to a low-frequency (<20 Hz) signal 704, a mid-frequency (20-150 Hz) signal 706, and a high-frequency (>150 Hz) signal 708.

Figure 34:
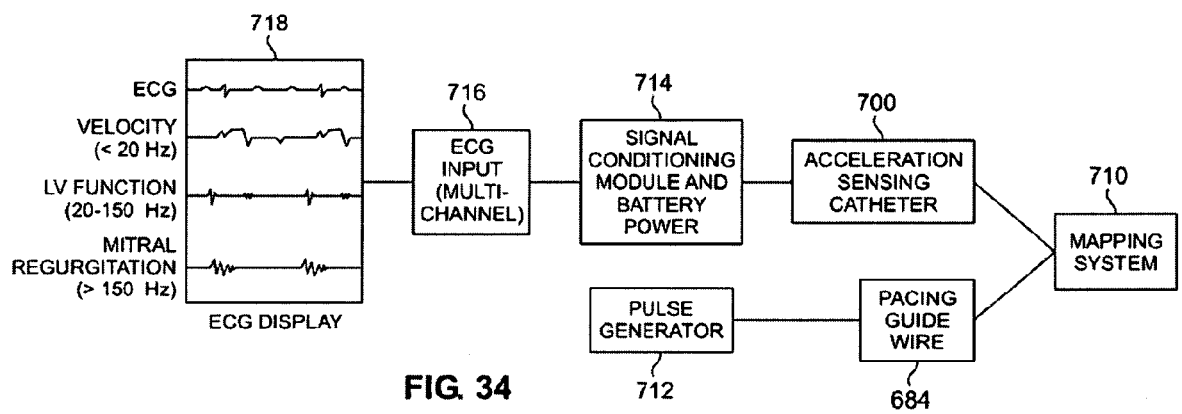

In this way, and referring to FIG. 34, the mapping system 710 is made of the acceleration sensing catheter 700 and the pacing guidewire 684. The pacing guidewire may be powered by a pulse generator 712.

The output of the sensors may be connected to a signal conditioning module and battery power module 714 prior to input into the electrogram recording 716 and display device 718. The output of the signal conditioning module may be analog signals if the electrocardiogram display is to be used. The signal conditioning module may also be used to correct or zero out the effects of gravity and the related tilt signal. Output from the signal conditioning module may also be digital. A microprocessing chip in the conditioning module may also perform functions such as forming a composite signal from multiple orientation axes and integration. The catheter within the guide catheter may have a guidewire lumen through which a pacing guidewire may be used to test pace target sites. This catheter may also have a port for contrast injection and may additionally have a balloon to perform an occlusive venogram.

The sensor catheter 700 may also have a curved tip (e.g., with a 90-degree bend) to facilitate access to tributary veins of the coronary sinus and great cardiac vein. The sensor catheter within the coronary guide catheter could also be moved from septal to lateral within the coronary sinus and great cardiac vein to identify general regions of dyssynchrony. The pacing wire could then be directed to the tributary veins of the coronary sinus or great cardiac veins or to the general region of delayed onset displacement motion. Variables such as the time from QRS onset to aortic valve closure (increase), peak acceleration during isovolumic contraction (increase), the length of the isovolumic contraction time interval (decrease), may be measured and are indicative of a favorable or therapeutic response and a more optimal LV or RV pacing region (FIG. 25). The changes in time intervals of LV cycle (e.g., LV filling time) may be normalized by dividing by the cardiac cycle length or the square root of the cardiac cycle length or by some other method. Other measures of LV function as sensed by the acceleration sensor may be utilized including favorable changes in the mitral regurgitation signal. The myocardial performance index (isovolumic contraction time plus the isovolumic relaxation time divided by the ejection time) may also be used as a performance indicator with decreases in indicator viewed as more favorable. When a region of improved LV function is identified, the pacing guidewire is left in place and the CRT LV lead is inserted over the pacing guidewire to the target pacing region.

Some patients may respond with favorable LV mechanics with only RV pacing if it is performed in the correct location. The optimal RV site to maximize LV function can be identified in the mapping strategy above. The acceleration sensor may reside in the coronary sinus while the RV pacing site is identified. This may eliminate the need for an LV lead in some patients.

Figure 35:
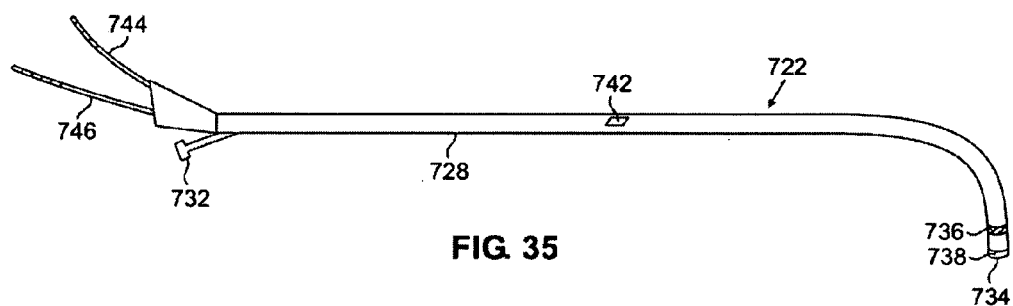
FIGS. 35-38 show a system for identification of a target pacing region and for optimizing and characterizing the pacing response.
Figure 36:
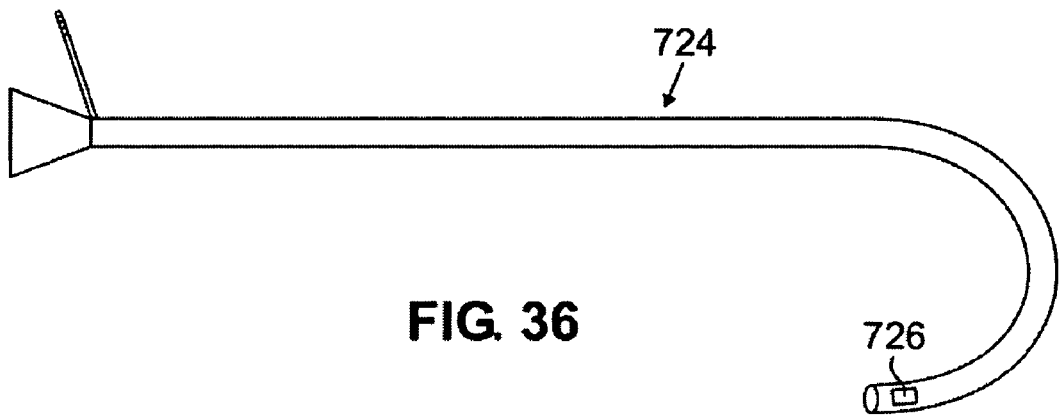

Alternative embodiments are apparent from the above description such as separating the higher frequency sensing accelerometer from the myocardial motion sensing accelerometer. Thus, referring to FIGS. 35 and 36, a system is shown for identification of the target pacing region and optimizing and characterizing the pacing response. The higher frequency sensing accelerometer may be incorporated into an LV lead or coronary guide catheter 724 or guidewire (see guide catheter 724 of FIG. 36). Guide catheters and guidewires are commonly used in CRT procedures. The acceleration sensor 726 on the guide catheter 724 may reside in the right atrium, at the coronary sinus ostium, or within the coronary sinus. The guide catheter 724 may be curved to facilitate access of the coronary sinus. Additionally, valve closure sensing may be performed externally with an acoustic sensing device.

Figure 37:
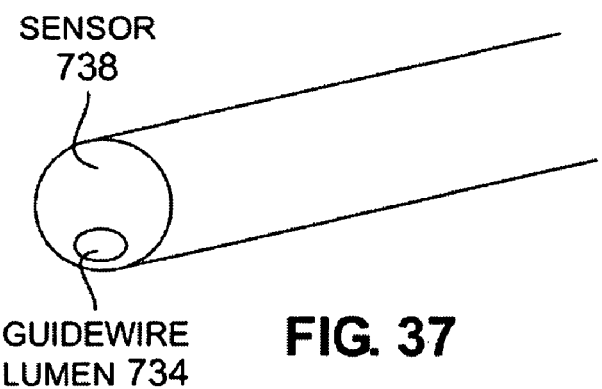
Figure 38:
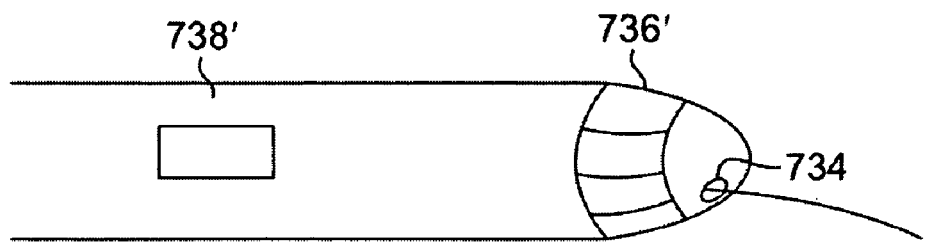
Figure 41:
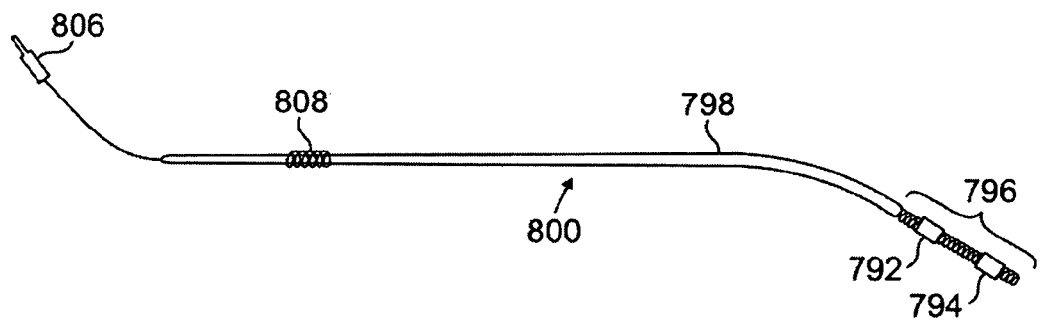
FIGS. 41-44 show a mapping system for optimizing and identifying target pacing regions.
Figure 42:
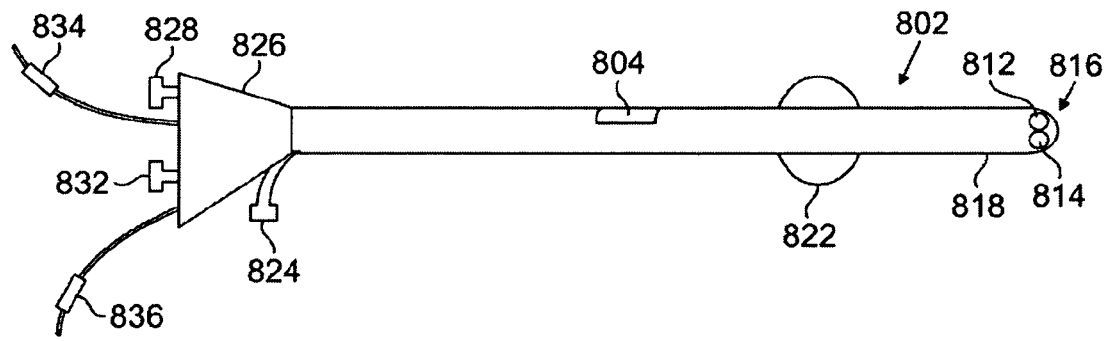

The remainder of the system may be the mechanical mapping catheter 722, which includes a guidewire lumen 728 with ports 732 and 734, a pacing electrode 736, acceleration sensor 738, e.g., one that is perpendicular to the catheter's longitudinal axis, an optional acceleration sensor 742, an electrode connector 744, and a sensor connector 746. The catheter 722 may be angled to facilitate LV vein cannulation. FIG. 37 shows one potential arrangement of sensor 738 and guidewire lumen 734. Alternatively, as shown in FIG. 38, an electrode 736' may be disposed at the distal tip of the catheter 722 while a sensor 738' is disposed proximal thereof.

Thus, in still another embodiment, and referring in particular to FIGS. 39 and 40, an acceleration sensor 752 for mid- to high-frequency sensing of the onset of systole and diastole and mitral regurgitation may be incorporated into a coronary sinus guide catheter 750. A set of conductive elements 748 for the sensor 752 may be coupled to a connector 754 that is used to connect to the microprocessor display.

A myocardial motion sensing accelerometer 746 is incorporated into a mapping catheter or LV lead 760. In the LV lead design, the conductive elements 754 for the low-frequency myocardial motion accelerometer 746 may be coupled to a proximal lead connector 758. The connector of the lead may be compatible with typical CRT IPGs (e.g., IS-1), although this is not necessary; in fact, the sensor connector and sensor signal may be designed to generally not interfere or even be read by the CRT IPG. Element 762 indicates the CRT pacing and sensing connector area. Connector 756 is also shown, which indicates a removable LV lead accelerometer connector for signal display.

Placement of the catheter is shown in FIG. 39, relative to the coronary sinus 770 and the coronary ostium 780. An optional pacing electrode 764 is shown, as well as guidewire, which may employ an integrated sensor for low-frequency myocardial motion sensing in the manner of FIG. 24.

During placement, the lead connector may be coupled to the acceleration sensor microprocessor display for visualizing myocardial motion signals and optimizing the LV lead placement. Alternatively, the LV lead sensor may be conductively coupled to a removable connector in the proximal lead portion, thus allowing the measurement of myocardial motion during lead placement. The LV lead sensor connector may also be capped after mapping and for long-term implantation. Alternatively, the sensors in this design may be RF MEMs accelerometers that are inductively-powered and which wirelessly transmit the data, thereby eliminating the need for conducting wires or elements.

FIG. 40A shows an embodiment of a guidewire-mounted sensor for use with the above guide catheter. In particular, guidewire 766 may have at a distal tip a soft tip 774, adjacent to which is a flexible coil section 768, within which is a sensor 772.

FIG. 40B shows an embodiment of an alternative LV lead design 790 or mapping catheter which may be used with the above guide catheter. LV lead 790 has at a distal tip a flexible coil 768' which terminates at a distal tip in a soft tip 774'. Within the flexible coil 768' is a sensor 772'. Electrode 776 may be provided adjacent to but proximal of the flexible coil 768'.

Referring to FIGS. 41-44, another alternative mapping device system and method for optimizing and identifying a target pacing region may include a venous guide sheath, a double lumen pacing catheter, and an acceleration sensing guidewire. The system also identifies the coronary ostium and coronary sinus vein branches using the accelerometer sensor.

A venous sheath 838 is used to gain access to the right atrium ("RA") via the subclavian or femoral vein. This sheath may include an optional mid- to high-frequency acceleration sensor 842. The sheath may have appropriate bends to facilitate entry into the coronary sinus.

A sensing guidewire with one or more sensors 792, 794, at least one being a lower-frequency sensor disposed on a highly flexible tip 796 (e.g., a coil tip 796), is placed into the RA via the sheath. The lower-frequency sensor may be multi-axis. An optional additional sensor may also be provided to sense low or high frequencies. The distance between the sensors may be, e.g., 5-10 mm. The sensor guidewire 800 is used to identify the coronary ostium (as above) by detecting the flow of blood into the RA and is then inserted into the coronary sinus. The guidewire 800 is shapeable or may have a slight bend 798 in the distal region, e.g., a 135 degree bend. The sensor guidewire 800 can then be positioned along the coronary sinus and into the LV veins for measuring myocardial deformation and velocity and comparing it to the reference point signal, i.e., vibrations related to isovolumic contraction/relaxation and/or valve closure, provided by the guide sheath sensor. Alternatively, a double lumen catheter 802 may be positioned into the RA or coronary sinus over the sensor guidewire 800 and an optional higher frequency sensor 804 on this device is used to provide reference signals.

The sensing guidewire 800 maps regions of late deformation, and may further include an electrical connector 806 and an optional proximal sensor 808 for sensing perivalvular events.

Figure 43:
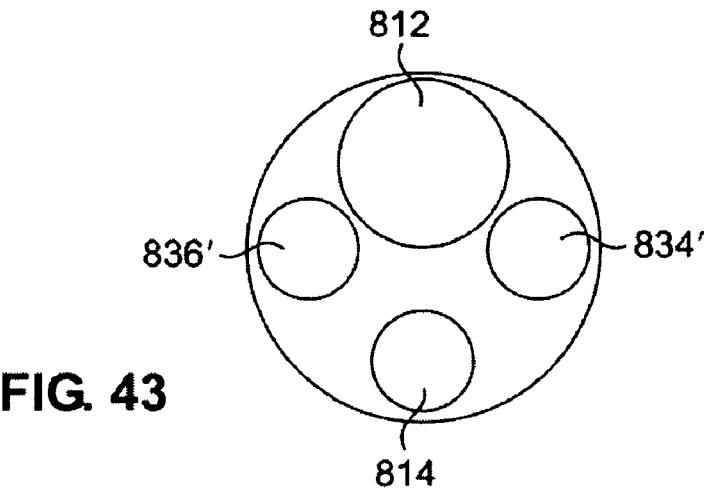
Figure 44:
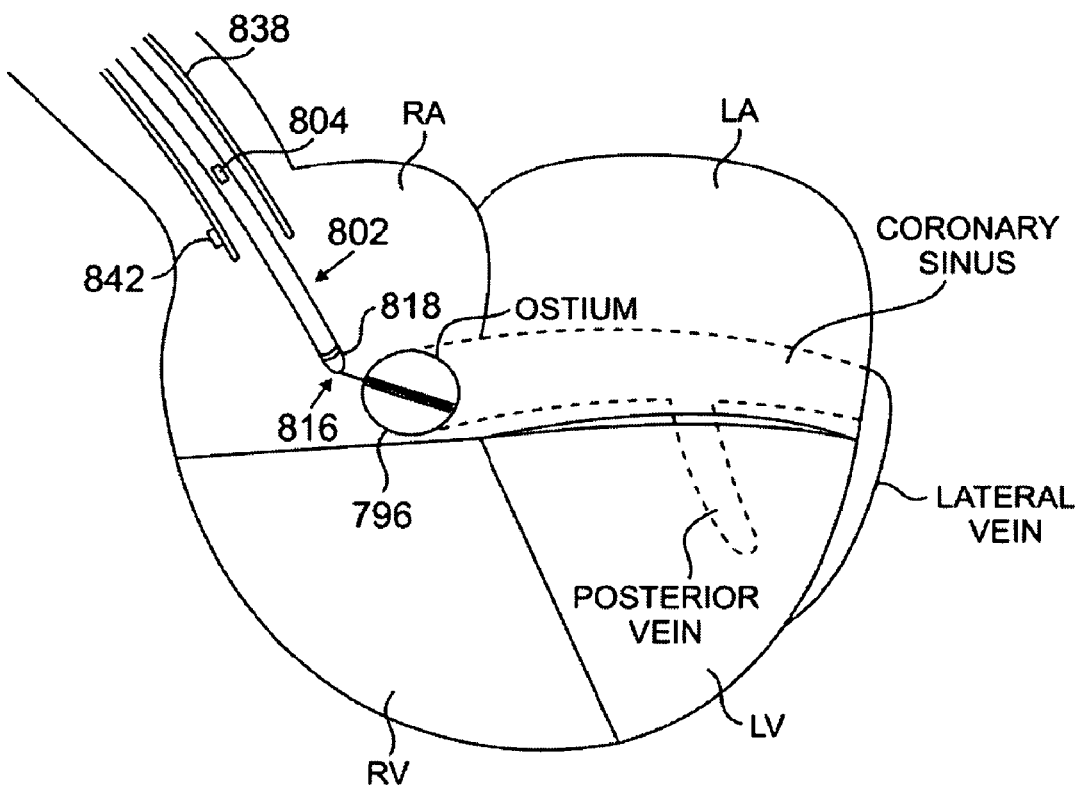

The double lumen pacing catheter 802 contains two guidewire lumens 812 and 814, lumen 812 serving as a guidewire sensor lumen and lumen 814 serving as a coronary wire sensor lumen, with openings in the distal tip 816, a pacing electrode 818, an optional coronary sinus occlusion balloon 822 with inflation port 824 for obtaining a venogram, optional acceleration sensors 804, such as for measuring high frequency signals, and the same may also be steerable. The overall diameter may be, e.g., 2-3 mm. Referring in addition to FIG. 43, a hub 826 may be provided with a sensor guidewire port 828, a coronary wire port 832, a high-frequency sensor connector 834 coupled to conductors within a lumen 834', and an electrode connector 836 coupled to conductors within a lumen 836'.

The double lumen pacing catheter is placed in the coronary sinus over the sensing guidewire. The venous guide sheath may be advanced into the ostium prior to double lumen catheter placement or LV lead placement. The balloon of the double lumen catheter may be inflated and a venogram obtained by injecting contrast though one of the catheter's lumens. After a target pacing region is identified in an LV vein with the sensor guidewire, the double lumen pacing catheter is advanced over the sensor guidewire to the region. Pacing is conducted with the double lumen pacing catheter and optimization of the target pacing site and intervals is carried out. A second guidewire for the LV lead is then advanced down the second lumen of the double lumen pacing catheter and into the target region. The pacing catheter and sensor guidewire are then removed, leaving the lead guidewire in place. The LV lead is then positioned into the target region over the second guidewire. With the double lumen configuration, the sensor guidewire can be made larger and more maneuverable without limiting the ability to place a small over-the-wire LV lead in the target region.

Myocardial motion mapping would be ideal for LV pacing that involves multiple electrodes. CRT may be optimized by pacing and early activation of all late deforming LV sites. Deformation mapping may identify these regions and then guide the placement of electrodes in the areas for CRT. Alternatively, if the mapping catheter is also the LV CRT lead, then the mapping lead may be left in the optimal location and connected to the IPG.

In the above catheter and implantable embodiments, miniaturization of the sensor is critical and wafer or die scale packaging of the sensor component is preferred. Consequently, where the MEMs sensor is attached by conductive elements to a connector and then to a microprocessor and/or display device, specific designs for attachment of the conductive elements to the silicon substrate of the wafer package chip must be utilized. It is particularly important to minimize the number of conductive elements that require attachment to the acceleration sensor. Potentially, at least 5 connections are required for a 3-axis sensor; however, using multiplexing circuitry or averaging the signal from all three sensors can eliminate two wires thus reducing the connections to three. In one embodiment, solder balls are integrated into the sensor die. A flex circuit with bonding pads that aligns with the solder balls is used for attachment to the die. The bonding pads of the flex circuit are in electrical communication with conductive elements that are used to attach to connectors at the proximal end of the catheter. The die part is flipped onto the bonding pad, which is heated to allow the flow of the solder and bonding of the die to the flex circuit.

Figure 45:
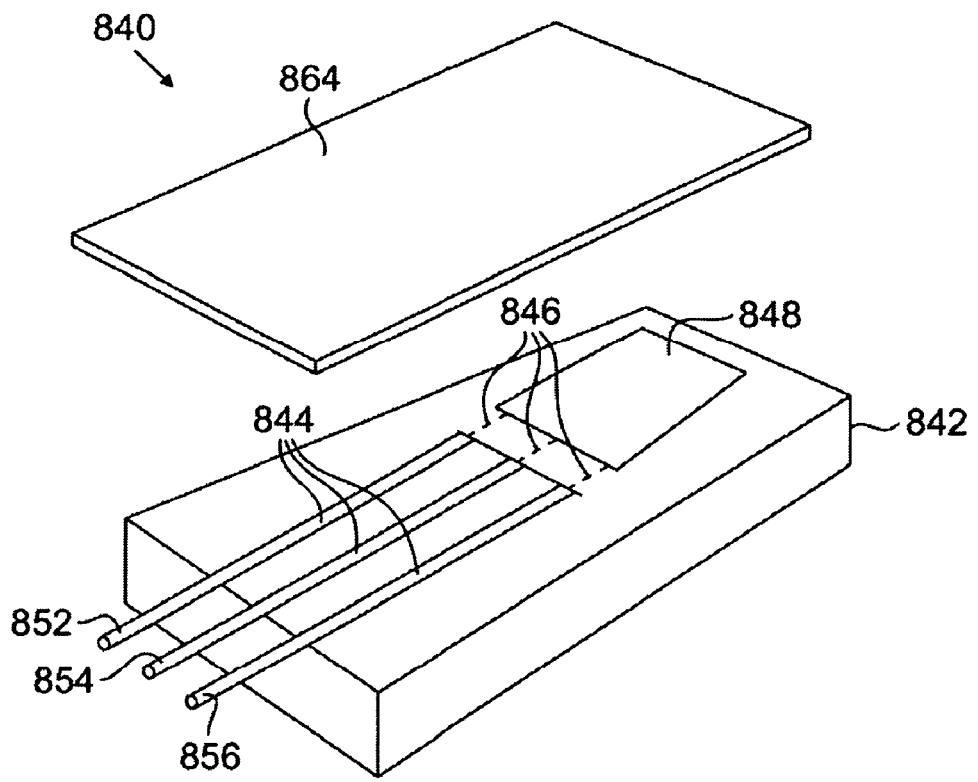
FIGS. 45-46 shows a system for wire attachment to a sensor chip which may be employed in the construction of a sensing catheter.
Figure 46:
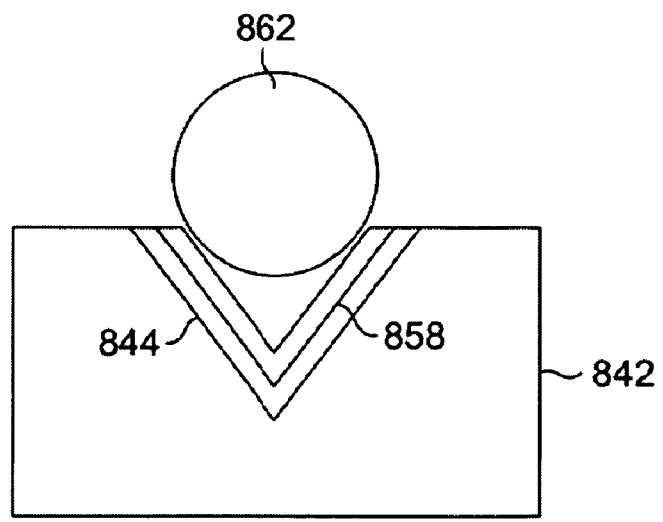

Alternative methods for conductive element attachment of MEMs sensors are provided in, e.g., U.S. Pat. No. 5,715,827 for a pressure sensor. FIGS. 45-46 show one potential embodiment to accomplish attachment for an acceleration sensor. The sensor chip 840 has an elongated silicon substrate 842. V or U-shaped via wells 844 are etched using silicon etching techniques into the elongated substrate 842. The wells 844 run the length of the elongated substrate 842 and abut against semiconductor output connectors 846 from the acceleration sensor integrated circuitry 848. Usually a sensor has three connectors: one for power, one for ground, and one for output. Additional connectors may be used for each axis output. A single output connector with a multi-axis sensor may have circuitry for multiplexing each axis output. Alternatively, the output may be an average or composite of the different axes. Hence three wells are etched and made continuous with the sensor circuitry for power 852, ground 854, and output 856. The silicon substrate well bottom and walls are doped to provide conductivity. The wells are then coated with metal 858 through a sputtering process or via other such processes. For example, a sputtered chromium and gold coating may be used. The uninsulated terminal length of small gauge copper wires 862 (e.g., 48 AWG) or a doped polymer flexible connector is then soldered to the wells. An epoxy or glass lid 864 or other such material, such as a wafer or polymer cap, may be bonded to the top of this chip/wire hybrid to protect the structure from damage. These wires or conductive polymers are now conductively coupled to the chip sensor and can be extended down the length of a catheter component and attached to a connector that will plug into a microprocessor data acquisition component.

Figure 47:
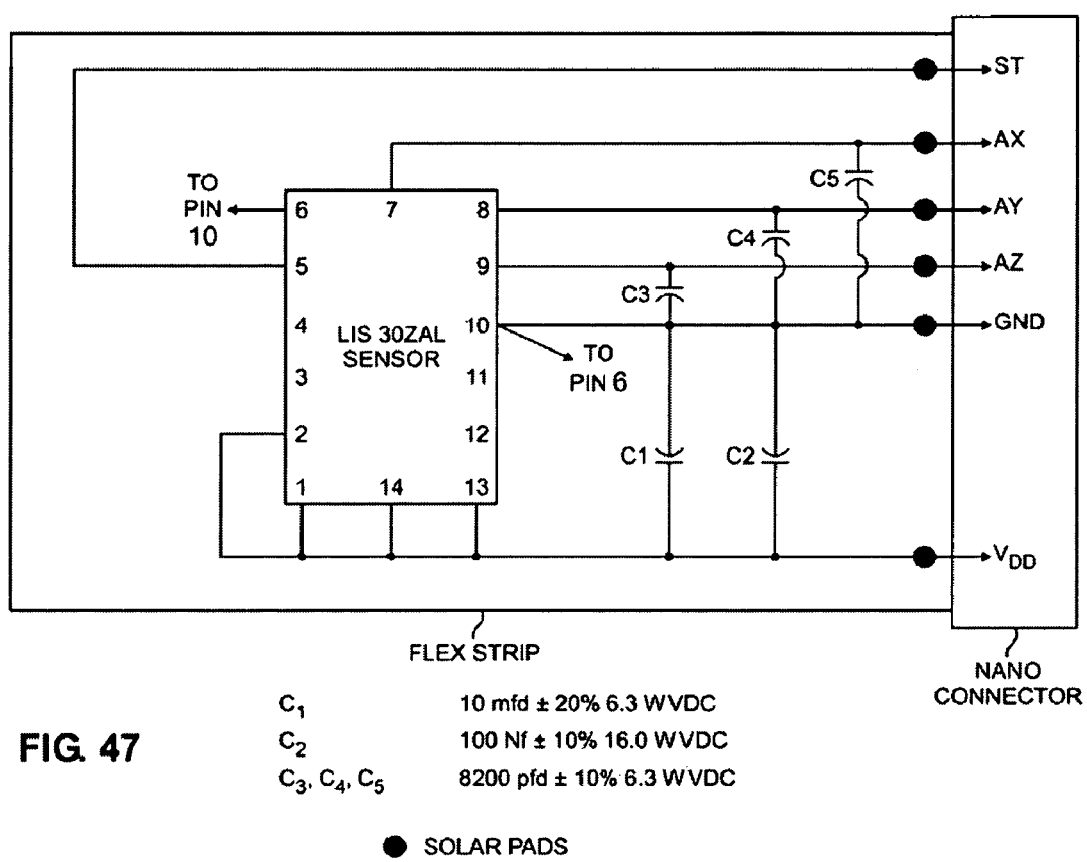
FIG. 47 shows a circuit diagram that may be employed in embodiments of the invention.

FIG. 47 shows a circuit diagram of a system that may be employed in embodiments of the invention. In particular, FIG. 47 shows a pin layout for a sensor chip that may be employed, along with the x-, y-, and z-outputs from the sensor chip.

Figure 48:
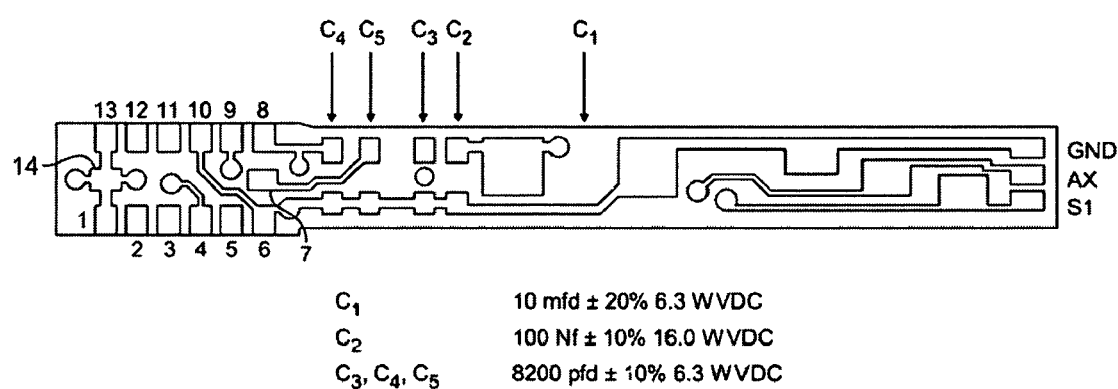
FIG. 48 shows a printed circuit board layout that may be employed in embodiments of the invention.

FIG. 48 shows a portion of a flexible circuit board that may employ the sensor chip. The sensor chip is mounted on the left side of the board, which is the portion that enters the patient. Capacitors C1-C5 are employed and are disposed directly adjacent the sensor chip as may be seen.

As noted above, the general design of the accelerometer sensors measures capacitance changes due to the movement of a proof mass beam with a side arm interdigitated between two capacitor plates. As the proof mass beam and side arm move with acceleration or vibration, the capacitance changes and this signal can be output as a measure of motion.

In this way, the sensor chip can measure extremely small changes in capacitance and thus acceleration. One of the functions of capacitors C1-C5 is to decouple certain voltages so that only signals from the sensor chip are registered at the signal analysis system (another is to provide the circuitry for the passband so that only a certain bandwidth of signals are passed). To ensure that a minimum of stray noise voltage is picked up by the conductive leads, capacitors C1-C5 are disposed as close to the chip as is practical, so that the signal travel distance is as short as possible.

It should be noted that the description above refers to specific examples of the invention, but that the scope of the invention is to be limited only by the scope of the claims appended hereto.

The invention claimed is:

1. A device for monitoring cardiac function, comprising:
 a. a single multi-axis acceleration sensor configured for disposition within the coronary sinus;
 b. wherein the acceleration sensor is configured to characterize left ventricular function by simultaneously monitoring both cardiac vibration corresponding to mitral regurgitation and left ventricular longitudinal displacement motion;
 c. a circuit implemented in hardware or software, or both, for receiving signals indicative of left ventricular function including signals corresponding to cardiac vibration caused by mitral regurgitation and signals corresponding to left ventricular longitudinal displacement motion, the circuit further mathematically singly integrating the received signals to obtain velocity information about left ventricular function and the circuit further mathematically doubly integrating the received signals to obtain displacement information about left ventricular function, wherein the single and double integrations are performed using only data from the single multi-axis acceleration sensor.

2. The device of claim 1, wherein the acceleration sensor is designed to detect vibrational frequencies between about 20 Hz and 150 Hz and displacement motion frequencies less than about 20 Hz.

3. The device of claim 1, wherein the acceleration sensor is designed to detect vibrational frequencies related to mitral regurgitation greater than about 150 Hz.

4. The device of claim 1, further comprising an endovascular catheter, and wherein the sensor is disposed on the endovascular catheter.

5. The device of claim 4, wherein the endovascular catheter is a coronary sinus catheter, and further comprising an occlusion balloon coupled to the catheter.

6. The device of claim 4, wherein the endovascular catheter is a coronary sinus catheter, and further comprising a pacing electrode coupled to the catheter guidewire lumen formed in the coronary sinus catheter.

7. The device of claim 1, further comprising an LV pacing lead, and wherein the sensor is disposed on the LV pacing lead.

8. A device for monitoring cardiac function, comprising:
 a. a catheter including a single three-axis acceleration sensor for disposition within the coronary sinus, wherein the acceleration sensor is configured to characterize left ventricular function by simultaneously monitoring both cardiac vibration corresponding to mitral regurgitation and left ventricular longitudinal displacement motion;
 b. a guide wire lumen formed within the catheter; and
 c. a circuit implemented in hardware or software, or both, for receiving signals indicative of left ventricular function including signals corresponding to cardiac vibration caused by mitral regurgitation and signals corresponding to left ventricular longitudinal displacement motion, the circuit further mathematically singly integrating the received signals to obtain velocity information about left ventricular function and the circuit further mathematically doubly integrating the received signals to obtain displacement information about left ventricular function, wherein the single and double integrations are performed using only data from the single multi-axis acceleration sensor,
 d. such that said device is configured to identify LV pacing regions.

9. A device for monitoring cardiac function, comprising:
 a. a catheter including a single three-axis acceleration sensor for disposition within the coronary sinus, wherein the acceleration sensor is configured to characterize left ventricular function by simultaneously monitoring both cardiac vibration corresponding to mitral regurgitation and left ventricular longitudinal displacement motion; and
 b. a circuit implemented in hardware or software, or both, for receiving signals indicative of left ventricular function including signals corresponding to cardiac vibration caused by mitral regurgitation and signals corresponding to left ventricular longitudinal displacement motion, the circuit further mathematically singly integrating the received signals to obtain velocity information about left ventricular function and the circuit further mathematically doubly integrating the received signals to obtain displacement information about left ventricular function, wherein the single and double integrations are performed using only data from the single multi-axis acceleration sensor, c. such that said device is configured to measure motion to characterize LV function.

* * * * *